(12) United States Patent
Kellenberger et al.

(10) Patent No.: US 7,524,823 B2
(45) Date of Patent: Apr. 28, 2009

(54) MACROLIDES

(75) Inventors: Johannes Laurenz Kellenberger, Basel (CH); Stuart Robert Shapiro, Kilchberg (CH); Salima Mathews, Basel (CH); Philippe Guerry, Binningen (CH); Pierre Jacques Noël Barbier, Rixheim (FR)

(73) Assignee: Basilea Pharmaceutica AG, Basel (CH)

( * ) Notice: Subject to any disclaimer, the term of this patent is extended or adjusted under 35 U.S.C. 154(b) by 359 days.

(21) Appl. No.: 11/429,678

(22) Filed: May 8, 2006

(65) Prior Publication Data

US 2006/0264387 A1     Nov. 23, 2006

(30) Foreign Application Priority Data

| Feb. 9, 2005 | (EP) | ................................. 05002664 |
| May 26, 2005 | (EP) | ................................. 05011419 |
| Feb. 8, 2006 | (CH) | ............... PCT/CH2006/000083 |

(51) Int. Cl.
*A61K 31/70* (2006.01)
*C07H 17/08* (2006.01)

(52) U.S. Cl. ........................................ 514/29; 536/7.4

(58) Field of Classification Search ....................... None
See application file for complete search history.

(56) References Cited

FOREIGN PATENT DOCUMENTS

| WO | WO02/16380 A1 | 2/2002 |
| WO | WO 03/072588 A1 | 9/2003 |
| WO | WO 2005/067969 A1 | 7/2005 |

OTHER PUBLICATIONS

International Search Report issued for the corresponding PCT application No. PCT/CH2006/000083.
Written Opinion of the International Search Report issued for the corresponding PCT application No. PCT/CH2006/000083.
Gorrini, et al., Inhibition of human neutrophil elastase by erythromycin and flurithromycin, two macrolide antibiotics, American Journal of Respiratory Cell and Molecular Biology. Oct. 2001; 25(4):492.
Culic et al., Anti-inflammatory Effects of Macrolide Antibiotics, European Journal of Pharmacology. Oct. 19, 2001; 429(1-3):209-229.
Bojar et al., Direct analysis of resistance in the cutaneous microflora during treatment of acne vulgaris with topical 1% nadifloxacin and 2% erythromycin, Drugs. 1995; 49 Suppl. 2:164-167.
M.T. Labro, Anti-inflammatory activity of macrolides: a new therapeutic potential? Journal of Antimicrobial Chemotherapy (1988) 41, Suppl. B, 37-46.

*Primary Examiner*—Elli Peselev

(57) ABSTRACT

The present invention relates to new antibiotic macrolide compounds of the general formula I:

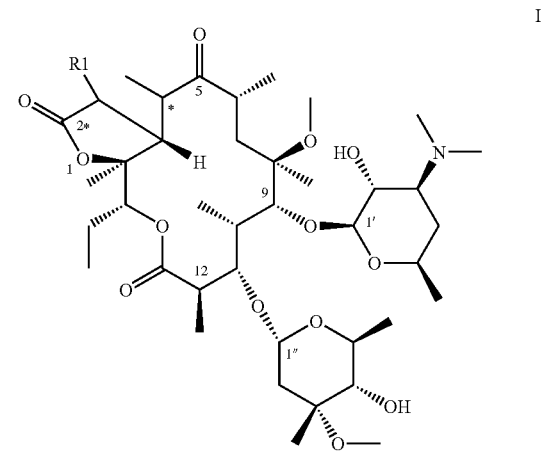

with improved activity, to medicaments comprising such antibiotics, and to the use of such antibiotics for the treatment of infectious diseases, inflammatory diseases and human diseases or disorders which can be ameliorated by inhibition human phospdiesterases.

15 Claims, No Drawings

MACROLIDES

CROSS-REFERENCE TO RELATED APPLICATIONS

This application claims priority from Patent Cooperation Treaty Application Number PCT/CH2006/000083, filed Feb. 8, 2006, which claims the priority of European Application Number 05011419.8, filed May 26, 2005, which claims the priority of European Application Number 05002664.0, filed Feb. 9, 2005.

BACKGROUND OF THE INVENTION

This invention relates to new macrolide antibiotics with improved activity, to medicaments comprising such antibiotics and to the use of such antibiotics for the treatment of infectious diseases and inflammatory diseases.

Macrolides are an effective and safe class of antibiotics. Among the commonly used macrolides are erythromycin, and the second generation agents clarithromycin and azithromycin. More recently the 3-keto macrolides, the so-called ketolides, have been developed that show improved activity towards macrolide-resistant bacteria.

Ketolides having a five-membered lactone ring fused to the macrolide ring have been disclosed in WO 02/16380, WO 03/072588, WO 02/50091, WO 02/50092, WO 03/024986 and US 2004/0038915. Macrolides having a five-membered lactone ring fused to the macrolide ring and a cladinose sugar attached to the macrolide ring have been disclosed in WO 03/042228 and in WO 03/004509. However, in WO 03/042228, the substitution of the cladinose sugar is different from the substitution of the compounds described hereafter, and in WO 03/004509, no sulfur atom is attached to the five-membered lactone ring.

Furthermore, macrolides have been reported to possess anti-inflammatory activity, and interest in the therapeutic potential of this anti-inflammatory activity has increased recently (e.g. Journal of Antimicrobial Chemotherapy, 1998, 41, Suppl. B, 37-46).

The invention provides new macrolide antibiotics of the following general formula I with improved biological properties:

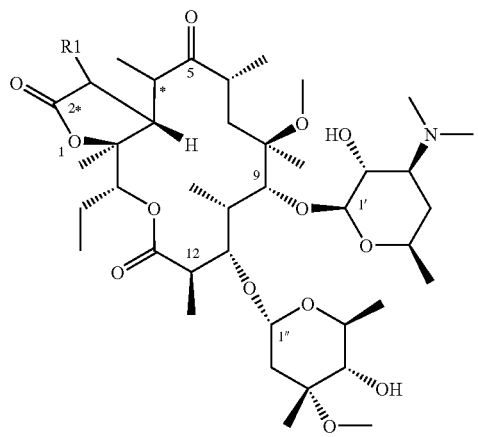

I wherein
R1 is a residue —Y—X-Q;
Y is S, SO or $SO_2$;

X is a bond or a linear group with up to 9 atoms consisting of C, N, O and/or S, of which up to 2 atoms can be N, one atom can be O or S, one carbon atom can appear as a CO group, one sulphur atom can appear as an $SO_2$ group and two adjacent C atoms can be present as —CH=CH— or —C≡C—;

Q is hydrogen, alkyl, heterocyclyl or aryl;

* indicates a chiral centre which is in the (R) or (S) form, i.e. including diastereomeric mixtures and separate stereomeric forms;

and pharmaceutically acceptable acid addition salts or in vivo cleavable esters thereof.

The compounds defined above are new and possess potent antimicrobial properties against Gram-positive and selected Gram-negative organisms. Therefore, they are useful as agents against Gram-positive pathogens such as staphylococci, streptococci, pneumococci and propionibacteria as well as some Gram-negative strains such as *H. influenzae* and may be used in human or veterinary medicine for treatment or prevention of infections caused by susceptible organisms including those resistant to erythromycin, clindamycin and tetracycline.

In addition to their antimicrobial properties they possess potent anti-inflammatory properties and may be used in human or veterinary medicine for treatment or prevention of inflammation.

As used herein the term "alkyl" refers to straight or branched chain saturated hydrocarbon group having 1 to 12 carbon atoms, preferably 1 to 6 carbon atoms. Such groups are for example methyl, ethyl, n-propyl, isopropyl, tertiary butyl, pentyl, hexyl, and the like. Such alkyl groups may be further substituted with one or more substituents selected from, for example, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined above, halogen substituted alkyl groups such as difluoromethyl or trifluoromethyl, trichloroethyl, cyano, nitro, amino, alkylamino, dialkylamino, alkylthio, mercapto, hydroxy, carbamoyl, a carboxyl group, an oxo group; or aryl or heterocyclyl as defined hereinbelow. The substituents can be identical or different from each other.

The term "halogen" refers to fluorine, chlorine, bromine or iodine.

The term "aryl" refers to aromatic groups with one or more preferably 6-membered aromatic nuclei and having from 6 to 14 carbon atoms. Examples are in particular phenyl, naphthyl, anthryl and phenanthryl. These groups may be further substituted with 1, 2, 3, 4 or 5 substituents selected from, for example, alkyl such as defined above, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined above, halogen substituted alkyl groups such as difluoromethyl or trifluoromethyl, trichloroethyl, cyano, nitro, amino, alkylamino, dialkylamino, alkylthio, mercapto, hydroxy, carbamoyl, a carboxyl group, an oxo group; or aryl or heterocyclyl as defined herein which may be unsubstitued or substituted with one or more of the above identified substituents other than aryl or heterocyclyl. The substituents can be identical or different from each other. In case more than one substituent is attached to the aryl group, these substituents can be identical or different from each other and are also encompassed by the scope of the present invention. For example dimethoxy-phenyl means that both methoxy substituents may be attached to the phenyl ring in the 2,3-position, the 2,4-position, the 2,5-position, the 2,6-position, the 3,4-position, the 3,5-position and the 3,6-position.

Examples of substituted aryl rings are p-methoxy-phenyl, 3,4-dimethoxy-phenyl, 3-cyclopentyloxy-4-methoxy-phenyl, 3-cyclopropylmethyloxy-4-difluoromethyloxy-phenyl, p-dimethylamino-phenyl, p-cyano-phenyl, 5-(dimethylamino)-1-naphthalenyl, 2,4-dimethoxyphenyl, 2'-methoxy-1,1'-biphenyl, 3,4-dimethylphenyl and 1,4-difluorophenyl.

As used herein the term "heterocyclyl" refers to an unsaturated or saturated, unsubstituted or substituted 5- to 10-membered (mono- or bicyclic) heterocyclic ring system containing at least one hetero atom selected from the group consisting of oxygen, nitrogen, and/or sulfur. Exemplary heterocyclic substituents include, but are not limited to, for example, the following groups:

piperidinyl, morpholinyl, 2-, 3- or 4-pyridyl, pyrrolidinyl, piperazinyl, 1H-pyrazol-1-yl, 1H-imidazol-1-yl, 1-H-imidazol-2-yl, pyrazinyl, pyrimidyl, pyridazinyl, pyrazolyl, triazinyl, thiazolyl, thiadiazolyl, oxadiazolyl, triazolyl, e.g. 1H-[1,2,4]-triazol-1-yl, 1H-tetrazolyl, 2H-tetrazolyl; thienyl, furyl (2-furanyl or 3-furanyl), 1H-azepinyl, tetrahydro-thiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiopanyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl (6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 2,6-diamino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 6-quinoxalinyl, 2-benzo[b]thien-3-yl, 3,4-dihydro-1H-2-oxo-quinolin-6-yl.

The heterocyclyl groups may be further substituted by one or more substituents. Such substituents include, for example, alkyl groups such as defined above, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined above, halogen substituted alkyl groups such as trifluoromethyl, trichloroethyl, nitro, amino, alkylamino, dialkylamino, alkylthio, mercapto, hydroxy, carbamoyl, a carboxyl group, an oxo group; or aryl or heterocyclyl as defined above which may be unsubstituted or substituted with one or more of the above-identified substituents other than aryl or heterocyclyl. In case more than one substituent is attached to the heterocyclyl group, these substituents can be identical or different from each other and are also encompassed by the scope of the present invention. For example dimethylpyridyl means that both methyl substituents may be attached to the pyridyl in the chemically possible positions. For example both methyl substituents may be attached to the 2-pyridyl in the 3,4-position, the 4,5-position, the 5,6-position, the 3,5-position, the 3,6-position, the and the 4,6-position. Both methyl substituents may be attached to the 3-pyridyl in the 2,4-position, the 2,5-position, the 2,6-position, the 4,5-position, the 4,6-position, the and the 5,6-position. Both methyl substituents may be attached to the 4-pyridyl in the 2,3-position, the 2,5-position, the 2,6-position, and the 3,5-position.

Examples of substituted heterocyclyl groups are 5-(2-pyridinyl)thien-2-yl, 2,4,6-trimethoxy-3-pyridinyl, 5-methyl-3-isoxazolyl, 5-cyanopyridin-2-yl; 6-(1H-imidazol-1-yl)-3-pyridinyl, 6-(1H-pyrazol-1-yl)-3-pyridinyl, 6-bromo-2-methyl-quinazolin-4-yl.

Especially preferred substituents for the heterocyclyl groups are alkyl, alkoxy, oxo, amino, alkylamino, dialkylamino or aryl, wherein alkyl, alkoxy and aryl are as defined hereinabove.

Examples of preferred substituted heterocyclic rings are 1H-pyrimidin-2,4-dione-1-yl, 1H,3H-pyrimidin-2,4-dione-5-methyl-1-yl, 1H-pyrimidin-4-amino-2-one-1-yl, 6-amino-9H-purin-9-yl, 6-dimethylamino-9H-purin-9-yl, 2,6-diamino-9H-purin-9-yl, 6-amino-8-[(3-pyridinylmethyl)amino]-9H-purin-9-yl, 4-phenyl-1H-pyrazol-1-yl, 3-(pyridin-3-yl)-1H-pyrazol-1-yl, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]triazol-1-yl, 3-(pyridin-4-yl)-1H-[1,2,4]triazol-1-yl and 2-oxo-1,2,3,4-tetrahydro-quinolin-6-yl.

In the combinations "heterocyclylalkyl" and "aralkyl" the components "heterocyclyl", "ar" (aryl) and "alkyl" have the meanings indicated above.

In a specific embodiment of the invention Q can be hydrogen or alkyl as defined above or a group of the following formula

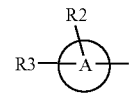

wherein

is a phenyl ring or a x-membered saturated or unsaturated heterocyclo-aliphatic or heteroaromatic ring containing from 2 to (x-1) carbon atoms with x being 5 or 6, and from 1 to 3 hetero atoms selected from the group consisting of nitrogen, oxygen and sulfur, R2 and R3 are independently selected from the group consisting of hydrogen, alkyl such as defined herinabove, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyoxy, halogen such as defined above, halogen substituted alkyl groups such as difluoromethyl or trifluoromethyl, trichloroethyl, cyano, nitro, amino, alkylamino, dialkylamino, alkylthio, mercapto, hydroxy, carbamoyl, a carboxyl group, an oxo group; or aryl or heterocyclyl as defined herein which may be unsubstitued or substituted with one or more of the above identified substituents other than aryl or heterocyclyl, or when both substituents R2 and R3 are located at adjacent carbon atoms of the ring

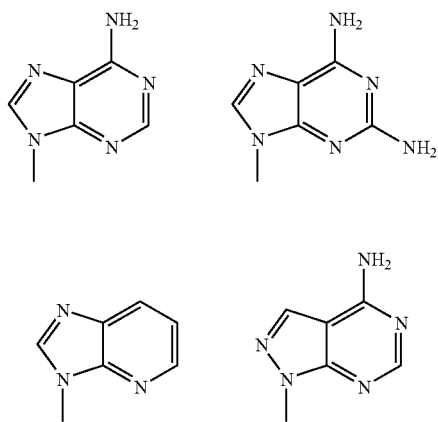

these two substituents can be taken together with said adjacent carbon atoms to form a 5 to 6 membered aromatic or a x-membered saturated or unsaturated heterocycloaliphatic or heteroaromatic ring containing from 2 to (X-1) carbon atoms with x being 5 or 6, and from 1 to 3 hetero atoms selected from the group consisting of nitrogen, oxygen and sulfur, whererin the residue Q can have alltogether one to four substituents of the kind defined above for R2 and R3.

Particularly preferred groups Q are, e.g.:

The symbol X represents a bond; i.e. is "absent", or is a spacer which is a linear group with up to 9 atoms and defined as above. The linear group with up to 9 atoms may carry additional hydrogen atoms, to saturate a C atom being a methylene group or to saturate a N atom being an amino group. Preferably, this spacer consists of 2 to 5 atoms.

Preferred groups X are:
$(CH_2)_n$, $(CH_2)_m OCH_2$, $(CH_2)_2 NCH_3 (CH_2)_2$, $CH_2 CH_2 NH$, and $(CH_2)_p COW$, where n and p are 1-3, m is 0-3 and W is absent or O or NH.

Particularly preferred groups X are ethyl and propyl.

Preferred groups Y are:

S, $SO_2$; particularly S.

Combinations of Y and X are:

For Y=S, X is ethyl, propyl, $CH_2CO$, $CH_2COCH_2$, $CH_2CONR$, $CH_2CONRCH_2$, $CH_2CONRCH_2CH_2$, $CH_2CH_2CONR$, $CH_2CH_2CONRCH_2$, $CH_2CH_2NR$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH=CH$ or $CH_2C\equiv C$;

where R in the above expressions is hydrogen or methyl.

Preferred groups $R^1$ are:

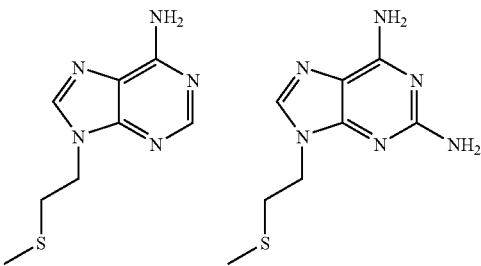

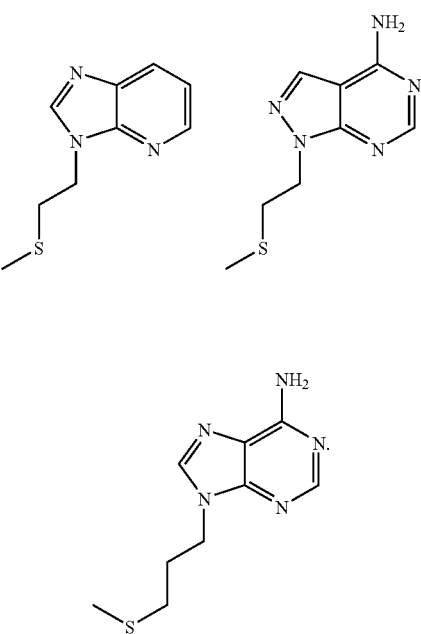

Also preferred are the following groups $R^1$:

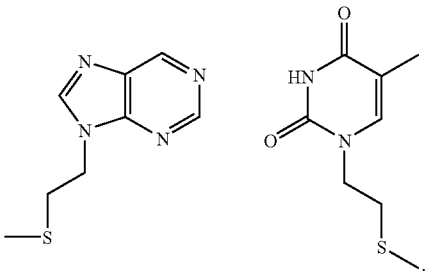

Concerning the two chiral centers indicated by * in the general formula I, the preferred configuration for these centers is 3S, 4R.

Preferred compounds of formula I are listed in the following Table 1:

TABLE 1
Formula I:
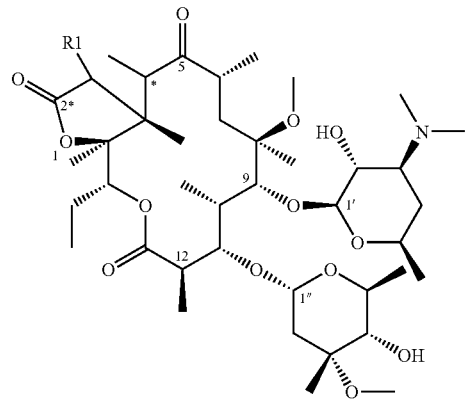
| Example | R₁ |
|---|---|
| 1 | 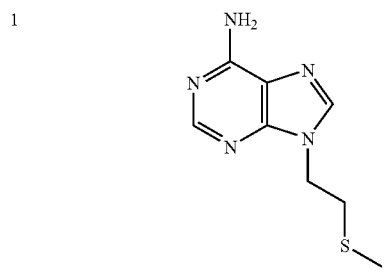 |
| 2 | 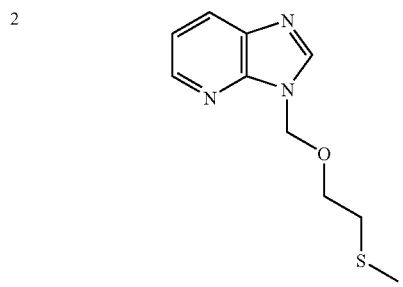 |
| 3 | 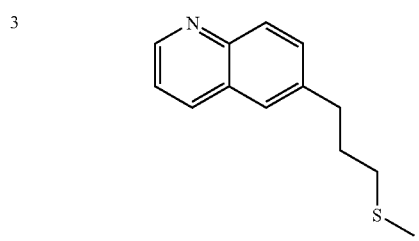 |
| 4 | 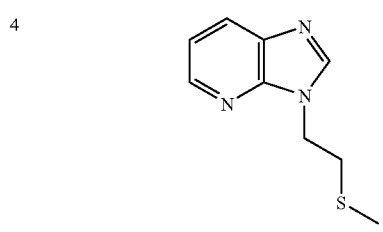 |
TABLE 1-continued
Formula I:
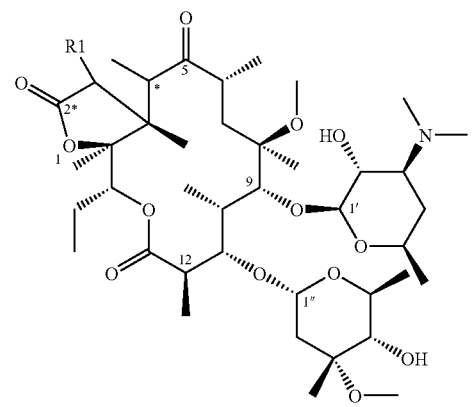
| Example | R₁ |
|---|---|
| 5 | 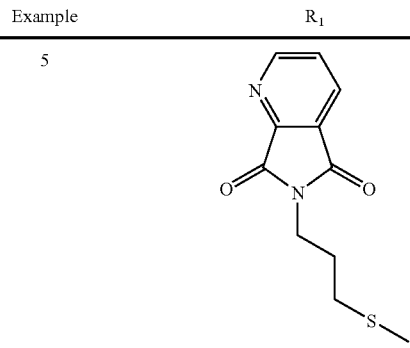 |
| 6 | 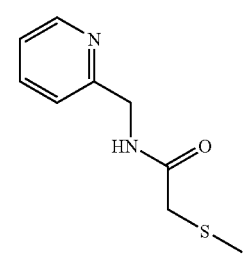 |
| 7 | 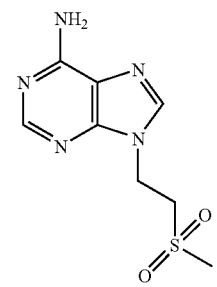 |
| 8 | 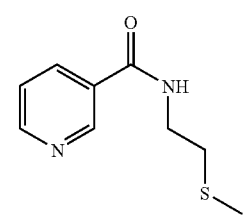 |

TABLE 1-continued

Formula I:

[Structure of Formula I macrolide with R1 substituent]

| Example | R₁ |
|---------|-----|
| 9 | 6-(methylthioethylamino)purine (N-H purine, CH₂CH₂SMe on amine) |
| 10 | 4-methoxybenzyl methylthio (4-MeO-C₆H₄-CH₂-S-Me) |
| 11 | 2,6-diamino-9-(2-(methylthio)ethyl)purine |
| 12 | 3-(imidazo[4,5-b]pyridin-1-yl)propyl methyl sulfide |
| 13 | 4-amino-1-(2-(methylthio)ethyl)pyrazolo[3,4-d]pyrimidine |
| 14 | 6-amino-9-(2-(N-methyl-N-(2-(methylthio)ethyl)amino)ethyl)purine |
| 15 | 2-(3-(methylthio)propyl)isoindoline-1,3-dione |

TABLE 1-continued

Formula I:

| Example | R₁ |
|---|---|
| 16 | 9-(3-methylthiopropyl)adenine |
| 17 | 3-(pyridin-3-yl)-1-(2-methylthioethyl)pyrazole |
| 18 | 1-(2-methylthioethyl)-1,2,4-triazole |
| 19 | 1-(2-methylthioethyl)benzimidazole |
| 20 | 9-(2-methylthioethyl)purine |
| 21 | 1-(2-methylthioethyl)thymine |
| 22 | N-(3,4-dimethylphenyl)-2-(methylthio)acetamide |
| 23 | N-(2,4-difluorophenyl)-2-(methylthio)acetamide |

TABLE 1-continued

Formula I:

| Example | R₁ |
|---------|-----|
| 24 | methyl 2-methoxy-4-[(methylsulfanyl)acetamido]benzoate |
| 25 | N-(quinolin-8-yl)-2-(methylsulfanyl)acetamide |
| 26 | 1-[4-(diethylamino)phenyl]-2-(methylsulfanyl)ethan-1-one |
| 27 | 1-(2,4-dimethoxyphenyl)-2-(methylsulfanyl)ethan-1-one |
| 28 | 1-(1-benzothiophen-3-yl)-2-(methylsulfanyl)ethan-1-one |
| 29 | 1-(1,3-benzodioxol-5-yl)-2-(methylsulfanyl)ethan-1-one |
| 30 | 2-amino-N-[2-(methylsulfanyl)ethyl]pyridine-3-carboxamide |
| 31 | 3,4-dimethoxy-N-[2-(methylsulfanyl)ethyl]benzamide |

TABLE 1-continued

Formula I:

| Example | R₁ |
|---|---|
| 32 | (6-amino-9-(2-(methylthio)ethyl)-8-((pyridin-3-ylmethyl)amino)-9H-purine) |
| 33 | (3-(cyclopentyloxy)-4-methoxy-N-(2-(methylthio)ethyl)aniline) |
| 34 | (N-(2-(methylthio)ethyl)-1-(pyridin-4-yl)methanamine) |

Particularly preferred are the compounds of Examples 1, 4, 11, 13 and 16.

If desired, compounds of formula I can be converted into a pharmaceutically acceptable acid addition salt. The salt formation is effected at room temperature with methods which are known per se and which are familiar to any person skilled in the art. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Further, the compounds can be converted into in vivo cleavable esters, for example into esters with the 2'-hydroxy group of the sugar moiety, such esters are e.g. acetates, pivaloyl esters, tartrates, maleates, succinates, and the like. These esters can be prepared according to methods known in the art, for example by reaction with an appropriate anhydride.

The compounds of the present invention and their pharmaceutically acceptable acid addition salts or in vivo cleavable esters thereof are useful as antibacterial and anti-inflammatory therapeutics. Compounds of formula I possess excellent antibacterial activity against selected pathogenic bacteria such as strains of *Staphylococcus aureus* and *Streptococcus pneumoniae*. They can thus be used as medicaments for the treatment of infectious diseases, especially of infections caused by staphylococci such as septicemia, skin and soft tissue infections, deep infections after trauma, surgery, or insertion of foreign material, endocarditis, pneumonia, arthritis, bursitis, and osteomyelitis; or infections caused by streptococci such as septicemia, skin and soft tissue infections, deep infections after trauma, surgery, or insertion of foreign material, endocarditis, tonsillopharyngitis, pneumonia, bronchopneumonia, bronchitis, otitis, sinusitis, and scarlet fever.

Furthermore compounds of formula I possess excellent antibacterial activity against selected bacteria such as strains of *Propionibacterium acnes* and *Propionibacterium granulosum*. They can thus be used as medicaments for the treatment of acne.

Furthermore, compounds of formula I can be used as medicaments for the treatment of infections caused by germs such as *Moraxella catarrhalis, Haemophilus* spp., *Neisseria* spp., *Legionella* spp., *Mycoplasma* spp., *Ureaplasma urealyticum, Rickettsia* spp., *Bartonella* spp., *Coxiella burnetti, Chlamydia* spp., or susceptible strains of *Mycobacterium* spp., *Nocardia* spp., and *Actinomyces* spp.

In addition to the antibacterial activity compounds of formula I possess anti-inflammatory activity, making them particularly useful for the treatment of diseases such as diffuse panbronchiolitis, cystic fibrosis, asthma, chronic obstructive pulmonary disease (COPD), inflammatory bowel diseases, rosacea, arthritis and inflammatory acne. The compounds of the present invention are also useful for the treatment of psoriasis.

The neutrophil granulocyte is a key element of the inflammatory process. The neutrophils migrate to the site of inflammation and can be activated to release toxic products, including proteolytic enzymes such as elastase. The initiation of the neutrophil response is mediated by cell surface receptors for chemoattractants including bacterial products, platelet activating factor, leukotriene B4, and interleukin 8. Elastase is a major secreted product of activated neutrophils and is a major contributor to the destruction of tissue in inflammatory disease. Several bioassays based on the repression of secretion of elastase, have been described and used for the detection of anti-inflammatory products (Johansson, S., Göransson, U., Luijendik T., Backlund, A., Claeson P., Bohlin L. (2002) J. Nat. Prod. 65: 32-41). As exemplified below (example 35), this test is used to show the modulatory activities of the compounds of the present invention against neutrophil granulocytes. The neutrophils are activated by addition of the bacterial product N-formyl methionyl-leucyl-phenylalanine (fMLP) and cytochalasin B, a stimulator of secretion. The amount of elastase secreted is determined by measuring the reaction of elastase with the chromogenic substrate succinyl-alanyl-alanyl-valyl-nitroanilide (SAAVNA), which generates 4-nitroaniline after cleavage by elastase. The reaction is followed by measuring the absorption change at 405 nm.

MIC values for non-anaerobes were obtained by broth microdilution using CAMHB (BBL) according to NCCLS guidelines (National Committee for Clinical Laboratory Standards. Methods for dilution antimicrobial susceptibility tests for bacteria that grow aerobically, 5$^{th}$ ed. Approved standard M7-A6. NCCLS, Wayne, Pa., 2003). Drugs were dissolved in DMSO prior to dispensing into 96-well microtitre plates; the concentration of DMSO in assay wells never exceeded 2% (v/v). CAMHB was supplemented with 5% (v/v) horse serum (Sigma, cat. no. H-1270) in lieu of laked horse blood for cultivation of *Streptococcus pneumoniae*, and with 5% (v/v) Fildes enrichment (BBL, cat. no. 220810) supernate in lieu of *Haemophilus* Test Medium and additives for cultivation of *Haemophilus influenzae* (Pankuch G A, Hoellman D B, Lin G, Bajaksouzian S, Jacobs M R, Appelbaum P C. Activity of HMR 3647 compared to those of five agents against *Haemophilus influenzae* and *Moraxella catarrhalis* by MIC determination and time-kill assay. Antimicrob. Agents Chemother. November 1998; 42(11): 3032-4). Activities expressed as the minimal inhibitory concentrations (MICs) (µg/ml) are given in the following Table 3, and the microorganisms used for testing are listed in Table 2 below.

concentration <0.1% was achieved by 2.5 h, and a $CO_2$ concentration >15% by 24 h. MIC values were read after incubation at 35-37° C. for 48 h (Table 3).

TABLE 2

| Microorganism | Code |
| --- | --- |
| *Staphylococcus aureus* ATCC 29213 | A |
| *Staphylococcus aureus* 1086 | B |
| *Escherichia coli* ATCC 25922 | C |
| *Streptococcus pneumoniae* 1/1 | D |
| *Streptococcus pneumoniae* SL199T | E |
| *Streptococcus pneumoniae* Tupelo | F |
| *Haemophilus influenzae* 12214 | G |
| *Haemophilus influenzae* QK50 | H |
| *Propionibacterium acnes* EG7NS | I |
| *Propionibacterium acnes* SW101T | K |

TABLE 3

| | MIC (µg/ml) | | | | | | | | | |
| --- | --- | --- | --- | --- | --- | --- | --- | --- | --- | --- |
| | A | B | C | D | E | F | G | H | I | K |
| Erythromycin | 0.5 | >32 | >32 | <=0.06 | >32 | 8 | 4 | 2 | 0.125 | >32 |
| Telithromycin | 0.25 | 0.25 | >32 | <=0.06 | <=0.06 | 0.5 | 2 | 1 | <=0.06 | 16 |
| Clindamycin | nd | nd | nd | nd | nd | nd | nd | nd | <=0.06 | >32 |
| Tetracycline | nd | nd | nd | nd | nd | nd | nd | nd | <=0.06 | 32 |
| Ex. 1 | 1 | >=32 | >=32 | <=0.06 | 0.125 | 0.5 | 1 | 0.5 | <=0.06 | 1 |
| Ex. 2 | 2 | 8 | >32 | <=0.06 | 0.5 | 0.5 | 4 | 8 | <=0.06 | 16 |
| EX. 3 | 4 | 8 | >32 | 0.25 | 2 | 8 | >32 | 16 | 0.25 | 16 |
| Ex. 4 | 1 | >=32 | 32 | <=0.06 | 0.5 | 0.5 | 2 | 2 | 0.125 | 4 |
| Ex. 5 | 2 | >32 | >32 | <=0.06 | 8 | 16 | 8 | 8 | <=0.06 | 16 |
| Ex. 6 | 0.5 | >32 | >=32 | <=0.06 | 1 | 2 | 2 | 2 | <=0.06 | >32 |
| EX. 7 | 32 | >32 | >32 | 2 | 4 | 16 | >32 | >32 | 2 | 8 |
| Ex. 8 | 1 | >32 | >32 | <=0.06 | 1 | 2 | 2 | 2 | <=0.06 | 16 |
| Ex. 9 | 4 | >32 | >32 | <=0.06 | 0.25 | 1 | 2 | 2 | 0.125 | 4 |
| Ex. 10 | nd | nd | nd | nd | nd | nd | nd | nd | nd | nd |
| Ex. 11 | 8 | >=32 | >=32 | <=0.06 | 0.125 | 1 | 2 | 2 | <=0.06 | 2 |
| Ex. 12 | 2 | 8 | >32 | <=0.06 | 0.5 | 1 | 4 | 8 | <=0.06 | 8 |
| Ex. 13 | 2 | 16 | >=32 | <=0.06 | 0.125 | 0.25 | 4 | 4 | <=0.06 | 2 |
| Ex. 14 | 2 | 16 | >32 | <=0.06 | 0.5 | 1 | 8 | 8 | <=0.06 | 16 |
| Ex. 15 | 1 | >=32 | >32 | <=0.06 | 1 | 2 | 4 | 4 | <=0.06 | 16 |
| Ex. 16 | 1 | >32 | >=32 | <=0.06 | 0.125 | 0.5 | 2 | 2 | 0.125 | 1 |
| Ex. 17 | 1 | >32 | >32 | <=0.06 | 0.5 | 1 | 4 | 4 | <=0.06 | 16 |
| Ex. 18 | 1 | >=32 | 32 | <=0.06 | 2 | 4 | 2 | 2 | <=0.06 | >32 |
| Ex. 19 | 1 | >32 | >32 | <=0.06 | 0.5 | 1 | 2 | 2 | <=0.06 | 4 |
| Ex. 20 | 1 | >32 | >32 | <=0.06 | 0.5 | 1 | 1 | 1 | <=0.06 | 8 |
| Ex. 21 | 2 | >32 | >32 | <=0.06 | 0.5 | 2 | 4 | 4 | <=0.06 | 4 |
| Ex. 22 | 2 | 32 | >32 | <=0.06 | 8 | 8 | 8 | 8 | <=0.06 | 32 |
| Ex. 23 | 2 | 32 | >32 | <=0.06 | 2 | 2 | 4 | 4 | <=0.06 | 32 |
| Ex. 24 | 1 | >=32 | >32 | <=0.06 | 4 | 8 | 8 | 8 | <=0.06 | >32 |
| Ex. 25 | 1 | 16 | >32 | <=0.06 | 1 | 0.5 | 4 | 4 | <=0.06 | 4 |
| Ex. 26 | 2 | >32 | >32 | 0.125 | >32 | >32 | >32 | 16 | 0.125 | >32 |
| Ex. 27 | 1 | >32 | >32 | <=0.06 | 4 | 4 | 8 | 8 | <=0.06 | >32 |
| Ex. 28 | 2 | 16 | >32 | 0.25 | 4 | 4 | 8 | 16 | 0.125 | 8 |
| Ex. 29 | 1 | >32 | 32 | <=0.06 | 4 | 4 | 4 | 4 | <=0.06 | >32 | nd = not determined

MIC values towards strains of propionibacteria were obtained by broth microdilution using WCB (Anaerobe Broth MIC, Difco) according to NCCLS guidelines (National Committee for Clinical Laboratory Standards. Methods for antimicrobial susceptibility testing of anaerobic bacteria, 5$^{th}$ ed.; approved standard. NCCLS publication no. M11-A5. NCCLS, Wayne, Pa., 2001). Microtitre plates were loaded into 7-L GENbox anaerobic incubation jars (BioMérieux, cat. no. 96 128) fitted with anaerobic atmosphere generators (BioMérieux, cat. no. 96 124) and a Dry Anaerobic Indicator Strip (BBL, cat. no. 271051). Under these conditions, an $O_2$ It has also been found that the compounds of the present invention exhibit substantial inhibitory activity towards human phosphodiesterases (PDEs), in particular towards PDE3 and especially PDE4, which have been shown to be involved in inflammatory processes (cf. e.g. Lipworth B. J., Lancet (2005) 365, p. 167 or Giembycz M. A., Curr. Opin. Pharmacol. (2005), 5, p. 238). This is shown in Examples 36 and 37 below, for the first time for a macrolide derivative like an erythromycin derivative. The use of the compounds of such macrolide derivatives, in particular of compounds according to the present invention for the treatment of diseases and disorders in humans which can be ameliorated or relieved by inhibition of human phodiesterases, in particular phosphodiesterase 3 and 4 (including inflammatory diseases as mentioned above) is therefore a further aspect of the present invention.

The compounds in accordance with the invention can be used as medicaments. They possess good oral absorption properties. A further embodiment of the present invention are thus medicaments comprising compounds of formula I, their pharmaceutically acceptable acid addition salts or in vivo cleavable esters thereof for the treatment and prevention of infectious diseases, for example, in the form of pharmaceutical preparations for enteral (oral) administration. The products in accordance with the invention can be administered, for example, perorally, such as in the form of tablets, film coated tablets, sugar coated tablets, hard and soft capsules, solutions, emulsions or suspensions, or rectally, such as in the form of suppositories, or parenterally e.g. by injection, or nasally, or by inhalation or transdermally, or locally for example by topical administration, preferably the compounds are administered topically or orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral, parenteral or topical dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

The compounds of formula I and their acid addition salts or in vivo cleavable esters thereof can be used for parenteral administration and for this purpose are preferably made into preparations for injection as lyophilisates or dry powders for dilution with customary agents, such as water or isotonic common salt solution.

The compounds of formula I and their acid addition salts or in vivo cleavable esters thereof can be used for topical administration and for this purpose are preferably made into preparations as ointments, creams or gels.

For the prevention and treatment of infectious diseases and/or inflammatory diseases in mammals, human and non-human, a daily dosage of about 10 mg to about 2000 mg, especially about 50 mg to about 1000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 100 mg, 250 mg, 500 mg and 1000 mg can be contemplated.

The reaction steps starting from known compounds leading to the end products of formula I are carried out according to schemes 1-3 below.

Scheme 1

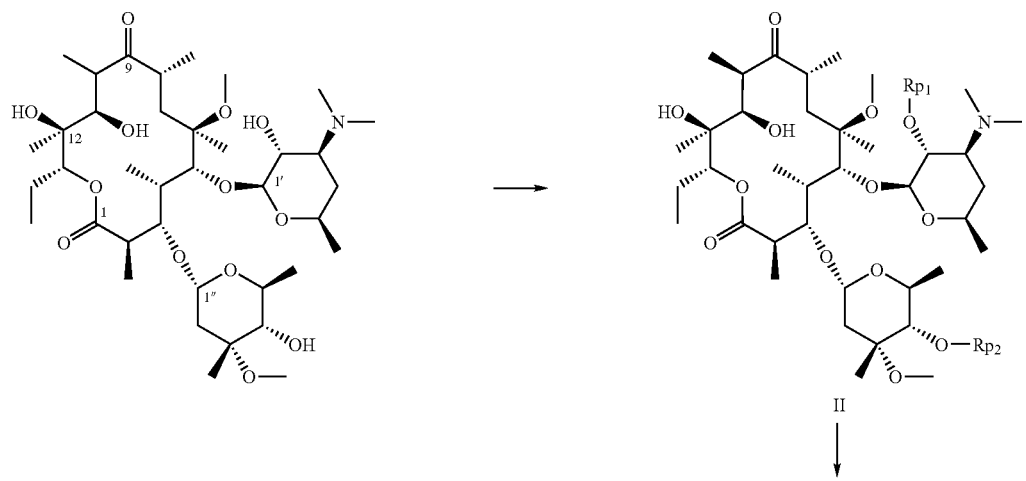

-continued

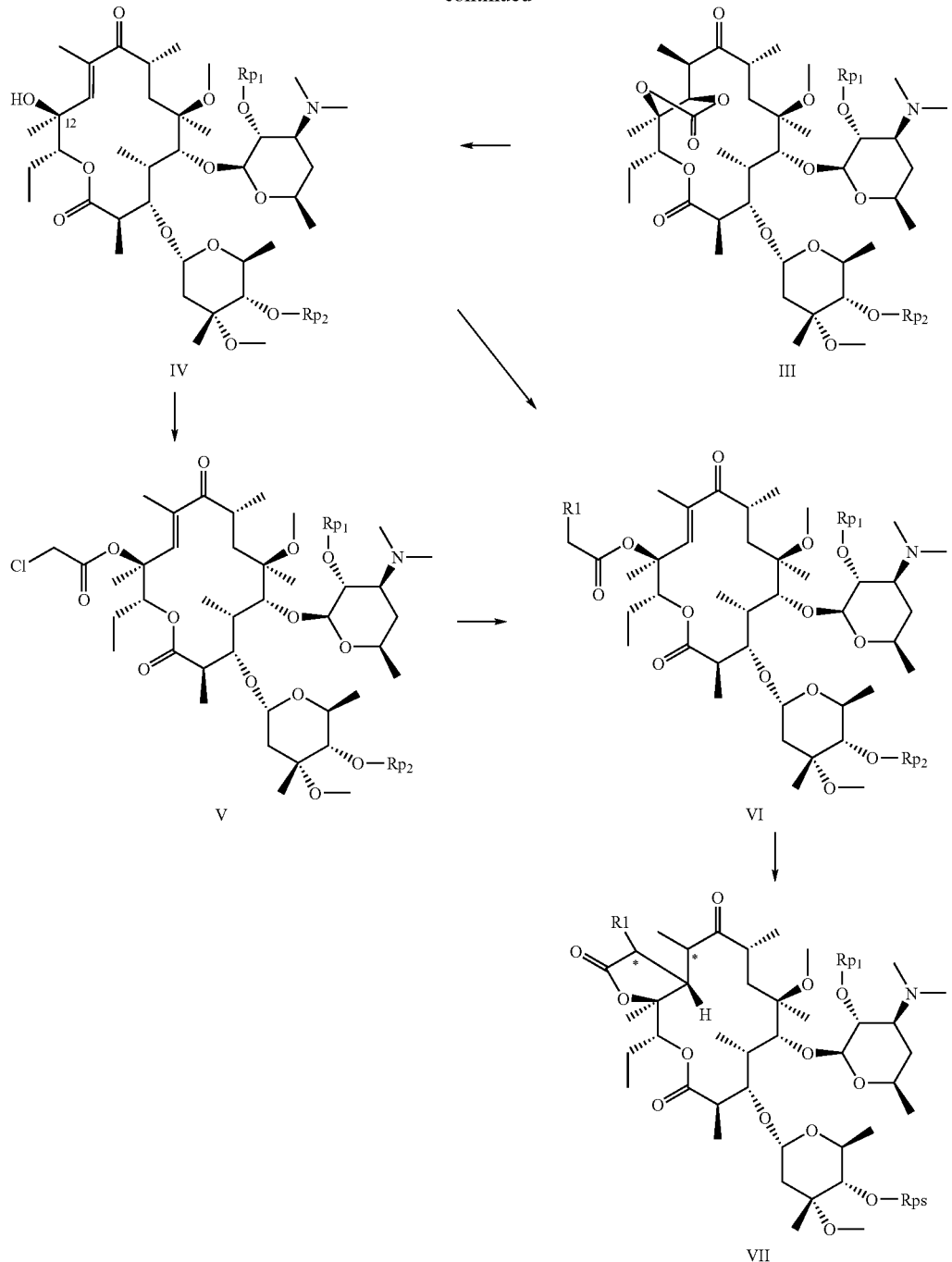

Compounds of the present invention can be prepared starting from clarithromycin. The preparation of compounds of formula II, III and IV wherein $Rp_1$ and $Rp_2$ are H, acetyl, benzoyl or any other suitable hydroxyl protecting group can be prepared by methods well known in the art (scheme 1). To obtain compounds of formula II wherein $Rp_1$ and $Rp_2$ are as defined above the 2'- and 4"-hydroxyl groups of commercially available clarithromycin can be protected either sequentially or simultaneously by reaction with a suitable acid anhydride or acid chloride as described in, for example, Baker et al., J. Org. Chem. 1988, 53, 2340-2345 and Kash- imura et al., J. Antibiotics, 2001, 54, 664-678. Compounds of formula II can then for example be transformed into compounds of formula IV in a similar way as described in Baker et al., J. Org. Chem. 1988, 53, 2340-2345.

The hydroxy group at position 12 of compounds of formula IV is esterified by treatment with 2-chloro acetic acid, DCC and DMAP or with 2-chloro acetic anhydride, pyridine, DMAP in a chlorinated solvent such as methylene chloride. The intermediate V is then treated with the appropriate nucleophile R1H in acetone in the presence of a base such as DBU to give compounds of formula VI wherein R1, $Rp_1$ and Rp$_2$ are as defined above. Depending on the nature of R1 compounds of formula VI can also be synthesised by reacting compound of formula IV with an appropriate carboxylic acid (R1CH$_2$COOH), DCC and DMAP in a chlorinated solvent such as methylene chloride to give compounds of formula VI. Compounds of formula VI are treated with an alkali metal base such as NaH or potassium tert.-butoxide or LDA in an aprotic solvent such as DMF or THF to give compounds of formula VII as mixture of diastereoisomers in various ratios (scheme 1).

Compounds of formula VII wherein R$_1$, Rp$_1$ and Rp$_2$ are as defined above are deprotected at the 2'-position with methanol at temperatures ranging from 20° C. to 60° C. during 2-5 days to give compounds of formula VIII (scheme 2). The 4"-hydroxyl group is deprotected by treatment of the compound with DBU in refluxing methanol for 3 to 12 hours (J. Antibiotics, 2001, 54(8), 664) or by treatment with guanidine/guanidinium nitrate in methanol/dichloromethane (Tetrahedron Letters 1997, 38(9), 1627) or with potassium carbonate in methanol or with a mixture of MeONa in methanol, preferably with DBU in refluxing methanol for 5 to 7 hours to give compounds of formula VIII.

Alternatively compounds of formula VII can be deprotected at the 2'- and the 4"-position simultaneously using one of the methods described above for the deprotection of the 4"-hydroxyl group to give compounds of formula I (scheme 2).

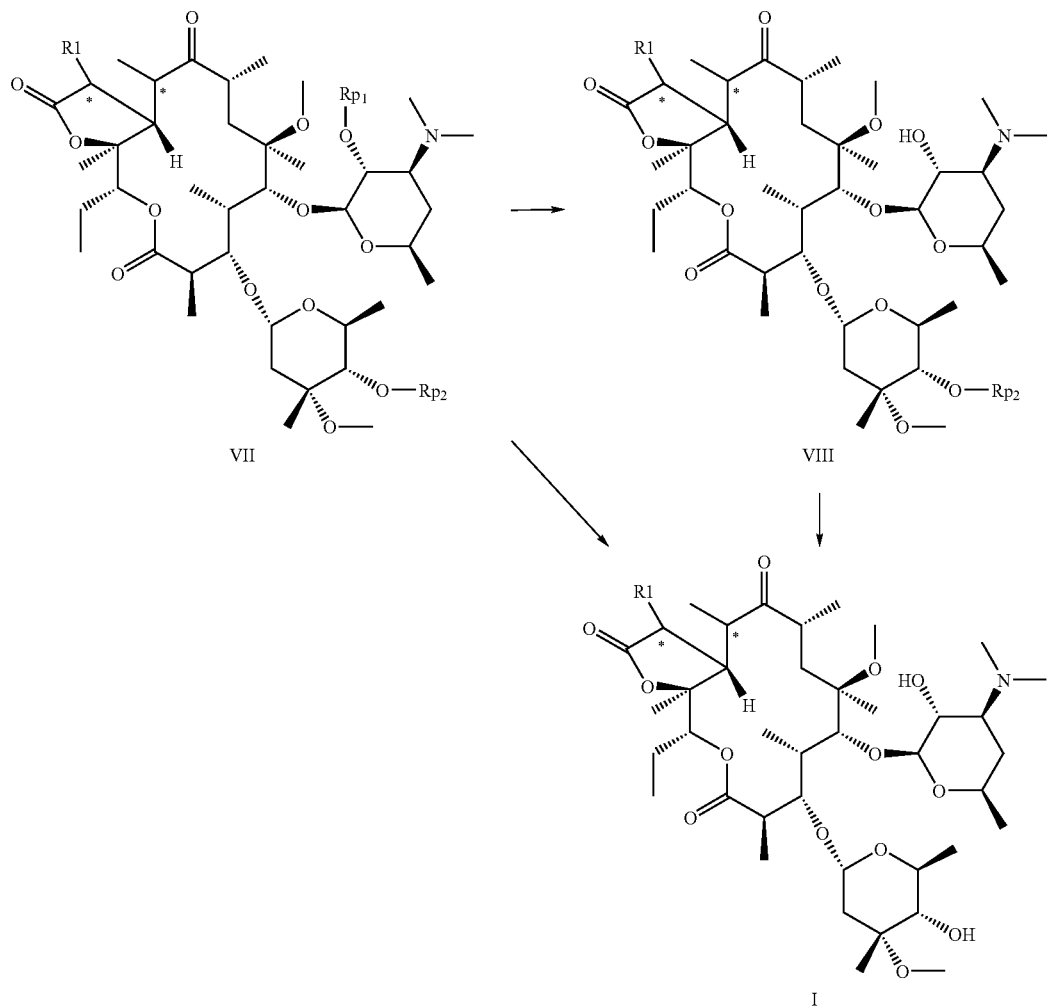

Scheme 2

In the case where R1 is S-Rp$_3$ and Rp$_3$ is a sulphur protecting group e.g. benzyl, 4-methoxybenzyl, 3,4-dimethoxybenzyl or 4-nitro-benzyl, preferably 4-methoxybenzyl the intermediate VIIa is transformed in the presence of molecular sieves into disulfide derivative IX wherein Rp$_1$ and Rp$_2$ are as defined above and Rp$_4$ is e.g. 3-nitro-2-pyridinyl or methyl similar to the method described in WO03/072588.

Compounds of formula IX are treated with a reducing agent such as a trialkyl phosphine, preferably tributyl phosphine, or a triaryl phosphine, preferably triphenyl phosphine, in a solvent such as aqueous acetone, aqueous dimethyl formamide, aqueous dioxane or aqueous tetrahydrofuran, preferably aqueous dimethyl formamide, at 0° C. to 60° C., preferably at room temperature for 1 minute to 1 hour, preferably 15 minutes, to give compound X. Compound X is treated, preferably without isolation, directly in the same solvent system with compounds of the formula Q-X-Lg, in which Q and X are defined as before and Lg is a leaving group, e.g. chloride, bromide, iodide, methanesulfonyloxy, p-tosylsulfonyloxy, trifluormethansulfonyloxy or a vinyl group in the case where X represents a carbonyl or a sulfonyl group to give compounds of formula VII. The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo[5.4.0]undec-7-ene or 1,5-diazabicyclo[4.3.0]non-5-ene, preferably 1,8-diazabicyclo[5.4.0]undec-7-ene at temperature between 0° C. and 50° C., preferably at 20° C. It can be advantageous to add catalytic amounts of an iodide salt, preferably sodium iodide, to the reaction mixture.

The following examples are given to further illustrate the invention and are not to be construed as in any way limiting the scope of the present invention.

General remarks: MS spectra were measured using (A) a Micromass Waters ZQ system with Masslynx software and (B) using a Q-Tof-Ultima (Waters AG) equipped with the Waters Cap-LC. For accurate mass determination the nano lock mass ESI source was used. Accurate masses are given with four decimal digits. HPLC purification of final products was done using the following system: Column: YMC ODS-AQ, 120A, 5 μm, 50×20 mm; precolumn: YMC ODS-AQ, 120A, 5 μm, 10×20 mm; flow: 30 ml/min; injection: 500 μl; detection: ELSD; mobile phase A: water+0.1% HCOOH; mobile phase B: acetonitrile; gradient: linear form 10 to 95% acetonitrile in 4 min. Abbreviations: HPLC for high performance liquid chromatography; DMSO for dimethylsulphox-

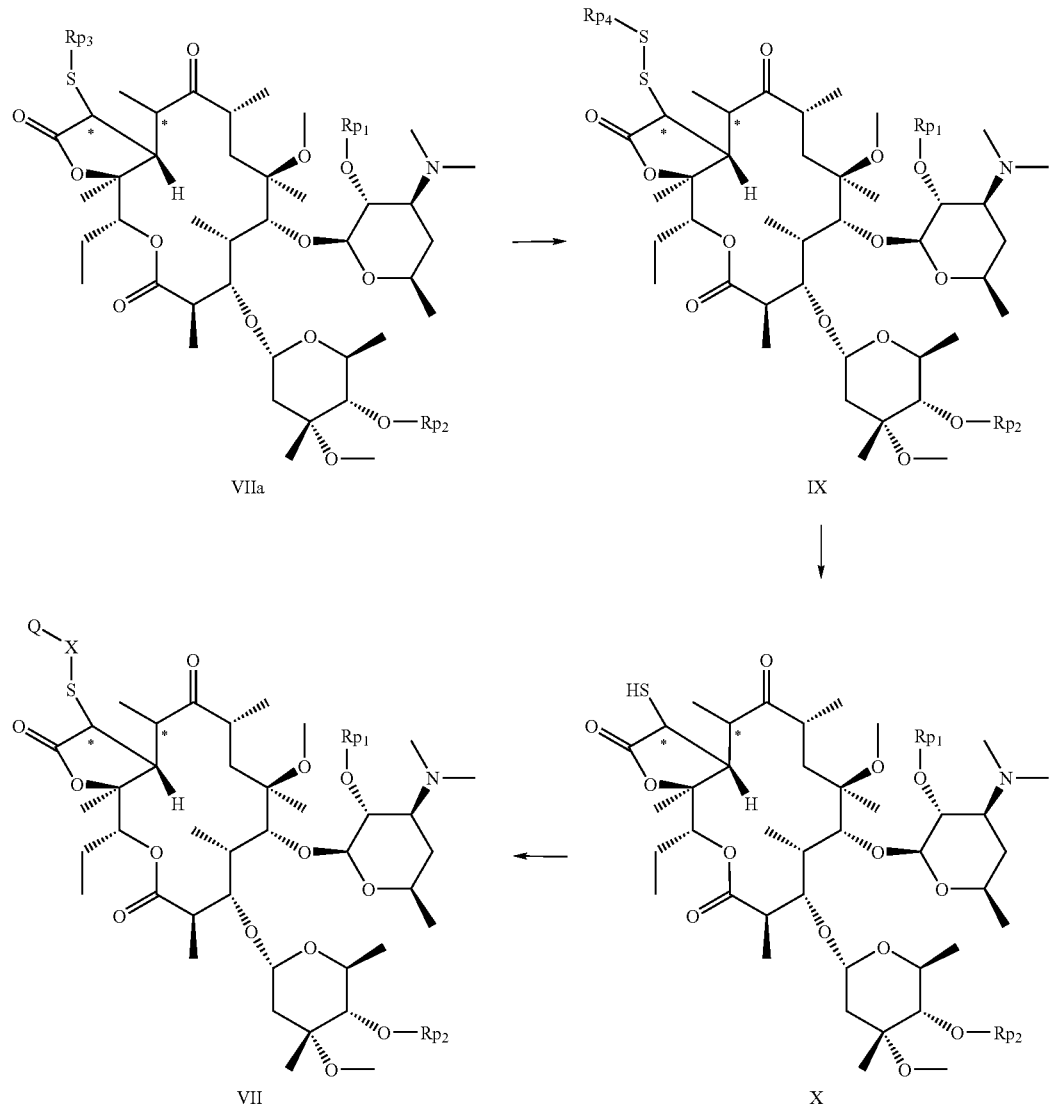

Scheme 3 ide; DBU for diazabicycloundecane; DCM for dichloromethane; DIPEA for diisopropylethylamine (Huenig's base); DMF for dimethylformamide; THF for tetrahydrofurane; DCC for dicyclohexylcarbodiimide; DMAP for 4-dimethylaminopyridine; EDC.HCl for N-(3-dimethylaminopropyl)-N'-ethylcarbodiimide hydrochloride; mCPBA for m-Chloroperbenzoic acid; KOtBu for potassium tert.-butylate; MS for mass spectrometry; NMR for nuclear magnetic resonance; ISP for ion spray.

EXAMPLE 1

Preparation of (3S, 3aR, 4R, 6R, 8R, 9R, 10S, 11S, 12R, 15R, 15aS)-3-[[2-[6-amino-9H-purin-9-yl]ethyl]thio]-11-[[2,6-dideoxy-3-C-methyl-3-O-methyl-α-L-ribo-hexopyranosyl]oxy]-15-ethyldecahydro-8-methoxy-4,6,8,10,12,15a-hexamethyl-9-[[3,4,6-trideoxy-3-(dimethylamino)-β-D-xylo-hexopyranosyl]oxy]-2H-furo [2,3-c] oxacyclotetradecin-2,5,13 (3H,6H)-trione (I-1), compound of formula I where R1 is [2-[6-amino-9H-purin-9-yl]ethyl] thio.

A] Preparation of 2',4"-Di-O-acetyl-6-O-methyl-erythromycin A (II-1) (compound of formula II where $Rp_1$ and $Rp_2$ are acetyl)

To a solution of 25 g (33.4 mmol) clarithromycin and 1.63 g (13.4 mmol) DMAP in 50 ml DCM were added 11 ml (117 mmol) acetic anhydride in one portion and the mixture was stirred for 20 h at room temperature. The reaction mixture was poured into enough 0.2 N NaOH to get a pH value of 8-9 and then extracted. The combined organic layers were washed with water and brine, dried over $MgSO_4$ and evaporated under reduced pressure. The crude product was crystallised from hot ethyl acetate to give 24.3 g (87%) of colorless crystals. MS(ISP): 832.5 [MH]$^+$ B] Preparation 2',4"-Di-O-acetyl-6-O-methylerythromycin A, 11,12 carbonate (III-1) (compound of formula III where $Rp_1$ and $Rp_2$ are acetyl)

24.3 g (29.2 mmol) of 2',4"-di-O-acetyl-6-O-methylerythromycin A were dissolved in 500 ml THF at −45° C. under argon and treated dropwise with 29.2 ml of a 1 M solution of sodium bis(trimethylsilyl)amide in tetrahydrofurane (29.2 mmol) over 15 min. After 20 min. at −45° C. 16.24 g (100.1 mmol) carbonyldiimidazole were added in 3 portions over 5 min. The reaction mixture was stirred at −45° C. for 30 min, then warmed to 0° C. over a period of 15 min and kept at 0° C. for 2.5 hours.

The reaction mixture was treated with a saturated aqueous solution of $NaHCO_3$ and water (1:1) and extracted twice with ethyl acetate. The combined organic layers were washed twice with 10% aqueous ammonia solution, with brine, dried over sodium sulfate and evaporated under reduced pressure to afford 23.57 g (94%) of a colorless solid. MS(ISP): 858.6 [MH]$^+$.

C] Preparation of 2',4"-Di-O-acetyl-10,11-didehydro-6-O-methylerythromycin A (IV-1) (compound of formula IV where $Rp_1$ and $Rp_2$ are acetyl)

23.5 g (27.47 mmol) of 2',4"-Di-O-acetyl-6-O-methyl-erythromycin A, 11,12 carbonate and 10.25 ml (68.7 mmol) DBU dissolved in 500 ml toluene were heated at reflux temperature for 1.5 h, cooled to room temperature and poured into 0.5 M aqueous $NaH_2PO_4$. The aqueous layer was extracted twice with ethyl acetate. The combined organic extracts were washed with 0.5 M $NaH_2PO_4$, brine, dried over $Na_2SO_4$ and concentrated to give 18.43 g (86%) of a colourless solid. MS (ISP): 814.5 [MH]$^+$.

D] Preparation of 10,11-didehydro-11-deoxy-6-O-methylerythromycin A, 2',4"-diacetate-12-(chloroacetate) (V-1) (compound of formula V where $Rp_1$ and $Rp_2$ are acetyl)

To a solution of 64.0 g (78.6 mmol) of 2',4"-Di-O-acetyl-10,11-didehydro-6-O-methylerythromycin A, 3.84 g (31.4 mmol) 4-dimethylaminopyridine and 12.5 g of pyridine in 600 ml dichloromethane was added dropwise a solution of 26.9 g of chloroacetic acid anhydride (157.3 mmol) in 250 ml dichloromethane over 2 hours under nitrogen. The solution was stirred at room temperature for 3.5 hours. The reaction mixture was poured into 0.2N NaOH to get to a pH value of 8-9 and extracted twice with dichloromethane. The combined organic layers were washed successively with water, twice with 0.5N $NaH_2PO_4$, with water and twice with brine, dried over $Na_2SO_4$ and evaporated to give crude product. Petroleum ether was added to the crude product, the mixture was stirred for 3 hours at room temperature and filtered to give the title compound (57.5 g, 82%) as a light brownish solid. MS (ISP): 890.3 [M]$^+$.

E] Preparation of compound of formula VI where R1 is [2-[6-amino-9H-purin-9-yl]ethyl]thio and $Rp_1$ and $Rp_2$ are acetyl) (VI-1)

9.79 g (10.99 mmol) compound of example 1 step D were dissolved under argon in 370 ml acetone and 1.73 ml DBU (11.54 mmol), 82.4 mg sodium iodide (0.55 mmol) and 2.43 g (6-amino-9H-purine)-1-ethanethiol (12.4 mmol) (WO0216380) were added. The reaction mixture was stirred under argon at room temperature over night. The solvent was evaporated and the residue was taken up in DCM. The organic layer was washed with 5% $NaHCO_3$, with brine, dried over $Na_2SO_4$ and evaporated in vacuo. The crude product was purified by flash chromatography on silica gel (DCM:MeOH:$NH_3$ 98:2:0.01→90:10:0.01) to give 6.85 g (59.4%) of a light brown foam. MS(ISP): 1050.4 [MH]$^+$; 526.4 [MH$_2$]$^{++}$).

F] Preparation of compound of formula VII where R1 is [2-[6-amino-9H-purin-9-yl]ethyl]thio and $Rp_1$ and $Rp_2$ are acetyl) (VII-1)

6.89 g (6.57 mmol) compound of example 1 step E were dissolved under argon in 40 ml DMF and cooled with an ice bath. 0.37 g sodium hydride (55-65%; 8.54 mmol) were added and the mixture was stirred during 4 hours at 0-5° C. Now aqueous $KH_2PO_4$ 0.5N were added and the mixture was extracted twice with diethyl ether. The combined organic layers were washed twice with 150 ml aqueous $NaHCO_3$ 5% and with 150 ml brine, dried over $Na_2SO_4$ and evaporated in vacuo to afford 7.05 g crude product. MS(ISP): 1050.3 [MH]$^+$; 526.2 [MH$_2$]$^{++}$).

G] Preparation of compound of formula I where R1 is [2-[6-amino-9H-purin-9-yl]ethyl]thio) (I-1)

7.0 g (6.5 mmol) of crude compound of example 1 step F were dissolved in 200 ml methanol and 4.99 ml (33.4 mmol) DBU were added. The mixture was heated to reflux under argon for 7 hours. The solvent was evaporated under reduced pressure and the residue was taken up in DCM. The organic layer was washed with aqueous NaHCO$_3$ 5% and with brine, dried over Na$_2$SO$_4$ and evaporated in vacuo. The crude product was purified by flash chromatography on silica gel (DCM: MeOH:NH$_3$ 95:5:0.01→85:15:0.01) to afford 4.50 g (69.9%) of the title compound as colourless solid as a single diastereoisomer. MS(ISP): 966.3 [MH]$^+$. $^1$H-NMR (CDCl$_3$): 0.85 (t, 3H), 1.11 (d, 3H), 1.13-1.27 (m, 15H), 1.29 (d, 3H), 1.45 (s, 3H), 1.47 (s, 3H), 1.51-1.95 (m, 8H), 2.29 (s, 6H), 2.29-2.48 (m, 5H), 2.58 (s, 1H), 2.59-2.68 (m, 1H), 2.82-2.89 (m, 1H), 3.01-3.10 (m, 2H), 3.06 (s, 3H), 3.11-3.23 (m, 2H), 3.32 (s, 3H), 3.46-3-54 (m, 2H), 3.57-3.65 (m, 1H), 3.68 (d, 1H), 3.75 (d, 1H), 3.97-4.02 (m, 1H), 4.42-4.58 (m, 3H), 4.67-4.75 (m, 1H), 4.85 (d, 1H), 5.37 (dd, 1H), 5.74 (s, br, 2H), 8.28 (s, 1H), 8.33 (s, 1H).

EXAMPLE 2

Preparation of compound of formula I where R1 is [2-[[3H-imidazo[4,5-b]pyridin-3-yl]methoxy]ethyl]thio (I-2)

A] Preparation of acetic acid 2-[(3H-imidazo[4,5-b]pyridin-3-yl)methoxy]-ethyl ester To a solution of 1.0 g (8.39 mmol) 3H-imidazo[4,5-b]pyridine in 20 ml DMF kept under argon at 0° C. 0.94 g (8.39 mmol) potassium tert-butoxide were added. The solution was warmed to room temperature and after 1 hour a solution of 1.74 g (8.8 mmol) (2-acetoxyethoxy)methyl bromide in 5 ml DMF was added dropwise over half an hour. The reaction was stirred at room temperature for 20 hours and then poured onto 75 ml of ice water. The mixture was extracted twice with 50 ml ethyl acetate. The combined organic layers were washed with water and brine, dried over Na$_2$SO$_4$ filtered and concentrated in vacuo. The crude product was purified by flash chromatography (silica gel, gradient DCM, DCM/MeOH 95/5 and 9/1) to afford 0.81 g (41%) of the desired product. MS(ISP): 236.2 [MH]$^+$.

B] Preparation of 2-[(3H-imidazo[4,5-b]pyridin-3-yl)methoxy]-ethanol 0.79 g (3.36 mmol) acetic acid 2-(3H-imidazo[4,5-b]pyridin-3-ylmethoxy)-ethyl ester were dissolved in 10 ml methanol and 10 mg (1.85 mmol) sodium methoxide were added. The mixture was stirred at room temperature for 3 hours. The orange mixture was concentrated in vacuo to afford 0.64 g (99%) of crude product. MS (EI): 193.2, 163.2, 148.2, 133.2.

C] Preparation of 3-(2-Chloro-ethoxymethyl)-3H-imidazo[4,5-b]pyridine

To a suspension of 0.63 g (3.26 mmol) 2-(3H-imidazo[4,5-b]pyridin-3-ylmethoxy)-ethanol and 1.71 g (6.52 mmol) triphenylphosphine in 10 ml pyridine kept under argon were added dropwise over 10 min. 0.32 ml (3.32 mmol) CCl$_4$. The suspension was stirred at room temperature for 18 hours and concentrated in vacuo. The crude product was purified by flash chromatography (silica gel, gradient DCM→DCM/MeOH 9/1) and triturated with diethylether to afford 0.7 g of a brownish solid. MS(ISP): 212.1 [MH]$^+$.

D] Preparation of thioacetic acid, S-[2-(3H-imidazo[4,5-b]pyridin-3-ylmethoxy)-ethyl] ester A suspension of 0.7 g (3.3 mmol) 3-(2-Chloro-ethoxymethyl)-3H-imidazo[4,5-b]pyridine and 378 mg (3.3 mmol) potassium thioacetate in 15 ml acetone was heated to reflux for 12 hours. The orange suspension was concentrated in vacuo. The crude product was purified by flash chromatography (silica gel, gradient of 0 to 10% methanol in DCM) to afford 380 mg (46%) of the desired product MS(ISP): 252.1 [MH]$^+$; $^1$H-NMR (CDCl$_3$): 2.28 (s, 3H), 3.05 (t, 2H), 3.69 (t, 2H), 5.72 (s, 2H), 7.27 (m, 1H), 8.09 (dd, 1H), 8.20 (s, 1H), 8.43 (dd, 1H).

E] 2-(Imidazo[4,5-b]pyridin-3-ylmethoxy)-ethanethiol 370 mg (1.47 mmol) thioacetic acid, S-[2-(3H-imidazo[4,5-b]pyridin-3-ylmethoxy)-ethyl] ester were dissolved in lo ml degassed methanol, kept under argon. Ammonia was bubbled through the solution for 5 minutes and the internal temperature rose to 40° C. The resulting solution was stirred for 60 minutes at room temperature and concentrated and dried at 60° C in vacuo to give the desired product. MS(ISP): 210.2 [MH]$^+$ The title compound I-2 was prepared starting from 2-(imidazo[4,5-b]pyridin-3-ylmethoxy)-ethanethiol and V-1 according to example 1 steps E-G. MS (ESI): 978.5238.

EXAMPLE 3

Preparation of compound of formula I where R1 is [3-[quinolin-6-yl]propyl]thio (I-3)

A] Preparation of 6-(3-Chloro-propyl)-quinoline 0.52 g (2.77 mmol) 3-quinolin-6-yl-propan-1-ol were dissolved in 5.5 ml thionylchloride and heated to 70° C. for 50 minutes. Water and aqueous sodium hydrogencarbonate were added and the mixture was extracted three times with DCM. The combined organic layers were washed with brine, dried over MgSO$_4$ and concentrated in vacuo to give 0.41 g (72%) of a brown oil. MS(ISP): 206.2 [MH]$^+$ B] Preparation of thioacetic acid S-(3-quinolin-6-yl-propyl) ester A solution of 0.41 g (2.0 mmol) 6-(3-chloro-propyl)-quinoline and 287 mg (2.5 mmol) potassium thioacetate in 8 ml acetone was heated to reflux for 8 hours. The mixture was concentrated in vacuo. The crude product was purified by flash chromatography (silica gel, gradient of 0 to 2% methanol in DCM) to afford 353 mg (71%) of dark orange oil. MS(ISP): 246.3 [MH]$^+$ C] Preparation of 3-Quinolin-6-yl-propane-1-thiol 450 mg (1.83 mmol) thioacetic acid S-(3-quinolin-6-yl-propyl) ester were dissolved in 15 ml degassed methanol, kept under argon. Ammonia was bubbled through the solution for 5 minutes and the internal temperature rose to 40° C. The resulting solution was stirred for 60 minutes at room temperature, concentrated and dried at 60° C. in vacuo to give 288 mg (77%) of the desired product. MS(ISP): 204.1 [MH]$^+$; $^1$H-NMR (CDCl$_3$): 1.40 (t, 1H), 2.00-2.08 (m, 2H), 2.58 (q, 2H), 2.94 (t, 2H), 7.35-7.40 (m, 1H), 7.55-7.60 (m, 2H), 8.01-8.12 (m, 2H), 8.86-8.88 (m, 1H).

The title compound 1-3 was prepared starting from 3-quinolin-6-yl-propane-1-thiol and V-1 according to example 1 steps E-G. MS(ESI): 972.5388.

EXAMPLE 4

Preparation of (3S, 3aR, 4R, 6R, 8R, 9R, 10S, 11S, 12R, 15R, 15aS)-11-[[2,6-dideoxy-3-C-methyl-3-O-methyl-α-L-ribo-hexopyranosyl]oxy]-15-ethyldecahydro-8-methoxy-4,6,8,10,12,15a-hexamethyl-3-[[2-[3H-imidazo[4,5-b]pyridin-3-yl]ethyl]thio]-9-[[3,4,6-trideoxy-3-(dimethylamino)-β-D-xylo-hexopyranosyl]oxy]-2H-furo [2,3-c] oxacyclotetradecin-2,5,13 (3H,6H)-trione (I-4) compound of formula I where R1 is [2-[3H-imidazo[4,5-b]pyridin-3-yl] ethyl]thio.

A] Preparation of 3-(2-Chloroethyl)-3H-imidazo[4,5-b]pyridine 6.5 g (54.56 mmol) 3H-imidazo[4,5-b]pyridine were dissolved under argon in 100 ml DMF and cooled to 0° C. in an ice bath. 4.6 g (109.1 mmol) sodium hydride were added and the mixture was stirred for 1 hour at room temperature. Then a solution of 9 ml (109.1 mmol) 1-bromo-2-chloroethane in 30 ml DMF was added over the period of an hour and the solution was stirred at room temperature during 20 hours. The brownish solution was poured onto ice water and extracted 3 times with ethyl acetate. The organic layers were combined, washed once with brine, dried over $Na_2SO_4$ and evaporated in vacuo to give a yellow oil. The oil was stirred with three times 50 ml warm heptane. Heptane was decanted, the tree fractions pooled and evaporated to give 2.08 g of light yellow crystals. MS(ISP): 182.2 $[MH]^+$; $^1$H-NMR ($CDCl_3$): 3.99 (t, 2H), 4.66 (t, 2H), 7.28-7.32 (m, 1H), 8.11-8.17 (m, 2H), 8.40-8.42 (m, 1H).

B] Preparation of compound of formula VIIa where $Rp_3$ is (4-methoxyphenyl)methyl and $Rp_1$ is acetyl and $Rp_2$ is hydrogen (VIIa-4)

2.0 g (2.16 mmol) of compound I-10 were dissolved in 50 ml DCM and 0.22 ml (2.4 mmol) acetic anhydride were added. The mixture was stirred at room temperature for 48 hours. The solution was washed with aqueous $NaHCO_3$ (5%) and brine, dried over $Na_2SO_4$, filtered and concentrated in vacuo to give 2.17 g of a light brown foam. The crude product was used without purification for the next step. MS(ISP): 967.3 $[MH]^+$.

C] Preparation of compound of formula IX where $Rp_4$ is methyl, $Rp_1$ is acetyl and $Rp_2$ is hydrogen (IX-4)

2.17 g (2.25 mmol) of the product of example 4, step B were dissolved in 50 ml DCM and molecular sieves was added. 880 mg (4.49 mmol) dimethyl(methylthio) sulfonium tetrafluoroborate were added to the mixture and the reaction was stirred for 5 hours at room temperature. The reaction mixture was filtered and washed twice with 20 ml aqueous $NaHCO_3$ (5%) and brine, dried over $Na_2SO_4$, filtered and concentrated in vacuo to give 1.62 g of a light brown foam. The crude product was used without purification for the next step. MS(ISP): 893.1 $[MH]^+$.

D] Preparation of compound of formula VII where R1 is [2-[3H-imidazo[4,5-b]pyridin-3-yl]ethyl]thio, $Rp_1$ is acetyl and $Rp_2$ is hydrogen (VII-4)

To a solution of 0.60 g (0.07 mmol) of the product of example 4 step C dissolved in 1 ml DMF and 1 drop of water 17 µl (0.07 mmol) of tributylphosphine were added and the mixture was stirred for 30 min at room temperature. Then 12.2 mg (0.07 mmol) of 3-(2-chloroethyl)-3H-imidazo[4,5-b]pyridine, 10 µl DBU (0.07 mmol) and some sodium iodide were added to the solution. The reaction was stirred for 4 hours at room temperature and concentrated in vacuo and the residue was taken up in DCM. The organic layer was washed with aqueous $NaHCO_3$ (3%) water and brine, dried over $Na_2SO_4$, filtered and concentrated in vacuo to give 150 mg of a yellow oil. The crude product was used without purification for the next step. MS(ISP): 992.3 ($[MH]^+$; 497.1 ($[MH_2]^{++}$).

E] Preparation of compound of formula I where R1 is [2-[3H-imidazo[4,5-b]pyridin-3-yl]ethyl]thio (I-4)

The crude product of example 4 step D (150 mg) was dissolved in 3 ml methanol and stirred for 72 hours at room temperature. Then reaction mixture was concentrated in vacuo and the residue was purified by HPLC to afford 22.2 mg (35%) of the desired product as a white solid as a single diastereoisomer. MS(ISP): 950.1 ($[MH]^+$; 476.0 ($[MH_2]^{++}$). $^1$H-NMR ($CDCl_3$): 0.85 (t, 3H), 1.1 (d, 3H), 1.14-1.22 (m, 9H), 1.23 (d, 3H), 1.25 (d, 3H), 1.29 (d, 3H), 1.46 (s, 3H), 1.48 (s, 3H), 1.52-1.59 (m, 2H), 1.65-1.71 (m, 1H), 1.75-1.95 (m, 3H), 2.20-2.35 (m, 2H), 2.3 (s, 6H), 2.40-2.48 (m, 1H), 2.59 (d, 1H), 2.62-2.70 (m, 1H), 2.81-2.90 (m, 1H), 2.99-3.11 (m, 2H), 3.08 (s, 3H), 3.17-3.26 (m, 2H), 3.32 (s, 3H), 3.45-3.53 (m, 2H), 3.63-3-71 (m, 2H), 3.75 (d, 1H), 3.95-4.02 (m, 1H), 4.45 (d, 1H), 4.52 (d, 1H), 4.58-4.66 (m, 1H), 4.80-4.88 (m, H), 5.38 (dd, 1H), 7.22 (dd, 1H), 8.05 (dd, 1H), 8.36 (dd, 1H), 8.57 (s, 1H).

EXAMPLE 5

A] Preparation of 6-(3-hydroxypropyl)-5H-pyrrolo[3,4-b]pyridine-5,7(6H)-dione To a suspension of 4.0 g (27 mmol) furo[3,4-b]pyridine-5,7-dione in 10 ml chloroform a solution of 2.03 g (27 mmol) of 3-aminopropanol in 7 ml chloroform was added and the mixture was heated to reflux for 30 minutes. Now the solvent was slowly evaporated and the mixture was gradually heated to 150-160° C. while the vacuum was maintained. After two hours the mixture was cooled to room temperature and the brownish crude product was purified by flash chromatography (silica gel, ethyl acetate/MeOH 15:1) to afford 3.9 g (70%) of the desired product as a white powder. $^1$H-NMR ($CDCl_3$): 1.89-1.95 (m, 2H), 2.25 (s, br, 1H), 3.64-3.68 (m, 2H), 3.90-3.96 (m, 2H), 7.60-7.66 (m, 1H), 8.14-8.20 (m, 1H), 8.93-8.99 (m, 1H).

B] Preparation of 6-(3-bromopropyl)-5H-pyrrolo[3,4-b]pyridine-5,7(6H)-dione

To a solution of 0.813 g (3.94 mmol) 6-(3-hydroxypropyl)-5H-pyrrolo[3,4-b]pyridine-5,7(6H)-dione in 10 ml acetonitrile were added dropwise 0.854 g (3.15 mmol) $PBr_3$ and the mixture was heated to reflux for 2 hours. The mixture was concentrated in vacuo and 6 ml of cold water were added to the residue. The precipitate was filtered, washed with cold water and dried in vacuo to get 0.71 g (71%) of the desired product as a light yellow powder. $^1$H-NMR (DMSO): 2.10-2.23 (m, 2H), 3.52-3.63 (m, 2H), 3.70-3.82 (m, 2H), 7.72-7.81 (m, 1H), 8.22-8.33 (m, 1H), 8.91-9.00 (m, 1H).

The title compound I-5 was prepared starting from 6-(3-bromopropyl)-5H-pyrrolo[3,4-b]pyridine-5,7(6H)-dione and IX-4 (compound of formula IX wherein $Rp_1$ is acetyl, $Rp_2$ is hydrogen and $Rp_4$ is methyl) according to example 4 steps D-E. MS(ESI): 991.5051.

EXAMPLE 6

Preparation of compound of formula I where R1 is [2-[(2-pyridinylmethyl)amino]-2-oxoethyl]thio (I-6)

A] Preparation of 2-Chloro-N-pyridin-2-ylmethyl-acetamide

To a solution of 0.5 g (4.6 mmol) 2-(aminomethyl)pyridine in 10 ml acetone at 0° C. were added 1.27 g (9.2 mmol) potassium carbonate and 0.57 g (5.1 mmol) 2-chloro acetyl-chloride. The reaction was stirred at 0° C. until no starting material remained and then poured onto ice water. The mixture was extracted twice with ethyl acetate. The combined organic layers were washed with aqueous $NaHCO_3$ (sat.) and brine, dried over $Na_2SO_4$, filtered and concentrated in vacuo. The crude product was used directly for the next step. MS(ISP): 185.21 ([MH]$^+$).

B] Preparation of compound of formula VII where R1 is [2-[(2-pyridinylmethyl)amino]-2-oxoethyl]thio, $Rp_1$ is acetyl and $Rp_2$ is hydrogen (VII-6)

To a solution of 0.50 g (0.06 mmol) of the product of example 4 step C dissolved in 10 ml DMF and 1 drop of water 27.7 μl (0.11 mmol) of tributylphosphine were added and the mixture was stirred for 3 hours at room temperature. Then 10.3 mg (0.06 mmol) of 2-chloro-N-pyridin-2-ylmethyl-acetamide dissolved in 1 ml DMF, 8.4 μl DBU (0.06 mmol) and a catalytic amount of sodium iodide were added to the solution. The reaction was stirred for 4 hours at room temperature and concentrated in vacuo and the residue was taken up in DCM. The organic layer was washed with aqueous $NaHCO_3$ (5%) water and brine, dried over $Na_2SO_4$, filtered and concentrated in vacuo. The crude product was purified by chromatography (silica gel, DCM: MeOH: $NH_3$ 98:2:0.01) to afford 36 mg of the desired product. MS(ISP): 995.31 ([MH]$^+$).

C] Preparation of compound of formula I where R1 is [2-[(2-pyridinylmethyl)amino]-2-oxoethyl]thio 34 mg (0.03 mmol) of compound VII-6 were dissolved in 10 ml methanol and stirred for 3 days at room temperature. The mixture was concentrated in vacuo and the residue was purified by HPLC to afford 16 mg (49%) of the desired product as a white solid as a single diastereoisomer. MS(ESI): 951.5101.

EXAMPLE 7

Preparation of compound of formula I where R1 is [3-[6-amino-9H-purin-9-yl]propyl]sulfonyl (I-7)

To a solution of 67 mg (0.07 mmol) I-16 (compound of formula I wherein R1 is [3-[6-amino-9H-purin-9-yl]propyl]thio) in 2 ml DCM at 0° C. were added 40 mg (0.48 mmol) sodium hydrogencarbonate and 59 mg (0.24 mmol) mCPBA. The mixture was stirred for two hours at 0° C. and for 3 hours at 5-10° C. and 5 ml of aqueous sodium pyrosulfite (10%) were added and stirred for another hour at room temperature. Aqueous $NaHCO_3$ was added and the mixture was extracted twice with DCM. The combined organic layers were washed with aqueous $NaHCO_3$ (5%) and brine, dried over $Na_2SO_4$, filtered and concentrated in vacuo. The crude product was purified by HPLC to afford 8 mg of the desired product as a single diastereoisomer. MS(ISP): 1012.4 ([MH]$^+$; 507.1 ([MH$_2$]$^{++}$)

EXAMPLE 8

Preparation of compound of formula I where R1 is [2-[(3-pyridinylcarbonyl)amino]ethyl]thio (I-8)

A] Preparation of compound of formula VII where R1 is (2-aminoethyl)thio and $Rp_1$ and $Rp_2$ are benzoyl (VII-8)

To a solution of 1.0 g (0.87 mmol) of compound of formula VII where R1 is [2-[[(1,1dimethylethoxy)carbonyl]amino]ethyl]thio and $Rp_1$ and $Rp_2$ are benzoyl (WO03072588) in 50 ml DCM at −10° C. kept under argon were added 1.51 ml (12.9 mmol) 2,6-lutidine and 1.56 ml (8.65 mmol) trimethl-silyl-trifluoromethanesulfonate and the mixture was stirred at −10 to 0° C. for two hours. The solution was poured into aqueous $K_2CO_3$ (5%) and the layers were separated. The organic layer was separated, dried over $Na_2SO_4$, filtered and concentrated in vacuo. The residue was dissolved in 20 ml THF at 0° C. and 1.3 ml of a solution of tetrabutylammonium fluoride in THF (1 M) was added. The resulting mixture was allowed to warm to room temperature. After 24 hours the mixture was concentrated in vacuo and the residue was taken up in DCM, washed with sat. aqueous $NaHCO_3$ and brine, dried over $Na_2SO_4$, filtered and concentrated in vacuo. The crude product was used without purification for the next step.

B] Preparation of compound of formula VII where R1 is [2-[(3-pyridinylcarbonyl)amino]ethyl]thio and $Rp_1$ and $Rp_2$ are benzoyl A solution of 11.5 mg (0.09 mmol) nicotinic acid, 46.6 mg (0.09 mmol) 1-benzo-triazolyloxytripyrrolidino-phosphonium hexafluorophosphate and 43.8 μl (0.26 mmol) N-ethyl-diisopropylamine in 10 ml THF was stirred for 15 minutes at room temperature. A solution of 90 mg (0.09 mmol) of the product of example 8 step A in 5 ml THF was added to the mixture and the reaction was stirred over the weekend at room temperature. The mixture was concentrated in vacuo and the residue was dissolved in DCM, washed twice with aqueous $NaHCO_3$ (5%) and brine, dried over $Na_2SO_4$, filtered and concentrated in vacuo. The crude product was purified by flash chromatography (silica gel, 1$^{st}$ column:

DCM:MeOH 98:2, 2$^{nd}$ column DCM:acetone 9:1) to afford 77 mg (77%) of the desired product as an amorphous solid. MS(ISP): 581.6 ([MH$_2$]$^{++}$).

C] Preparation of compound of formula I where R1 is [2-[(3-pyridinylcarbonyl)amino]ethyl]thio (I-8)

A solution of 77 mg (0.07 mmol) of the product of example 8 step B and 49 µl (0.33 mmol) DBU in 10 ml methanol was heated to 75° C. during 5 days. The mixture was concentrated in vacuo and the crude product was purified by HPLC to afford 16 mg (25%) of the desired product as a white solid as a single diastereoisomer. MS(ISP): 953.3 ([MH]$^+$; 477.6 ([MH$_2$]$^{++}$).

EXAMPLE 9

Preparation of compound of formula I where R1 is [2-[(1H-purin-6-yl)amino]ethyl]thio(I-9)

A] Compound of formula I where R1 is [2-[[(1,1-dimethylethoxy)carbonyl]amino]ethyl]thio A solution of 0.5 g (0.43 mmol) of the compound of formula VII where R1 is [2-[[(1,1-dimethylethoxy)carbonyl] amino]ethyl]thio and Rp$_1$ and Rp$_2$ are benzoyl (WO03072588) and 0.32 ml (2.16 mmol) DBU in 10 ml methanol was heated to reflux during 5 days. The mixture was concentrated in vacuo and the residue was dissolved in DCM, washed with aqueous NaHCO$_3$ (5%) and brine, dried over Na$_2$SO$_4$, filtered and concentrated in vacuo. The crude product was used directly for the next step. MS(ISP): 948.5 ([MH]$^+$).

B] Preparation of compound of formula I where R1 is (2-aminoethyl)thio

The desired product was obtained from the product of example 9 step A following the procedure described in example 8 step A. the crude product was used without purification for the next step.

C] Preparation of compound of formula I where R1 is [2-[(1H-purin-6-yl)amino]ethyl]thio (I-9)

To a solution of 350 mg of the crude product of example 9 step B in 15 ml acetonitrile were added 69 µl triethylamine and 70 mg 6-chlorpurine. The mixture was heated to reflux during 4 days. The mixture was concentrated in vacuo and the residue was dissolved in DCM, washed with aqueous NaHCO$_3$ (5%) and brine, dried over Na$_2$SO$_4$, filtered and concentrated in vacuo. The crude product was purified by HPLC to afford the desired product as a single diastereoisomer. MS(ISP): 966.6 ([MH]+; 484.1 ([MH$_2$]$^{++}$).

The following products listed in Table 4 were prepared according to the examples described above:

TABLE 4

| Ex | R1 | Prepared according to example | MS |
|---|---|---|---|
| 10 | [(4-methoxyphenyl)methyl]thio | 1 | 925.48 |
| 11 | [2-(2,6-diamino-9H-purin-9-yl)ethyl]thio | 1 | 979.5351 |
| 12 | [3-(3H-imidazo[4,5-b]pyridin-3-yl)propyl]thio | 1 | 962.5254 |

TABLE 4-continued

| Ex | R1 | Prepared according to example | MS |
|---|---|---|---|
| 13 | [2-(4-amino-pyrazolo[3,4-d]pyrimidin-1-yl)ethyl]thio | 1 | 964.5141 |
| 14 | 3-[[[2-(6-amino-9H-purin-9-yl)ethyl]methylamino]ethyl]thio | 1 | 1021.5794 |
| 15 | [3-(1,3-dioxo-1,3-dihydro-isoindol-2-yl)propyl]thio | 4 | 990.5087 |
| 16 | [3-(6-amino-9H-purin-9-yl)propyl]thio | 4 | 978.5341 |
| 17 | [2-[3-(3-pyridinyl)-1H-pyrazol-1-yl]ethyl]thio | 4 | 974.5292 |
| 18 | [2-(1H-1,2,4-triazol-1-yl)ethyl]thio | 4 | 898.4956 |
| 19 | [2-(1H-benzimidazol-1-yl)ethyl]thio | 4 | 949.5 |
| 20 | [2-(9H-purin-9-yl)ethyl]thio | 4 | 951.4 |
| 21 | [2-(5-methyl-2,4-1H-pyrimidinedion-1-yl)ethyl]thio | 4 | 957.4 |
| 22 | [2-(3,4-dimethylphenyl-amino)-2-oxoethyl]thio | 6 | 964.5283 |
| 23 | [2-(2,4-difluorophenyl-amino)-2-oxoethyl]thio | 6 | 972.4841 |
| 24 | [2-(3-methoxy-4-methoxycarbonyl-phenylamino)-2-oxoethyl]thio | 6 | 1024.5165 |
| 25 | [2-(quinolin-8-ylamino)-2-oxoethyl]thio | 6 | 987.518 |
| 26 | [2-[4-(diethylamino)-phenyl]-2-oxoethyl]thio | 4 | 992.5646 |
| 27 | [2-(2,4-dimethoxyphenyl)-2-oxoethyl]thio | 4 | 981.507 |
| 28 | [2-(benzo[b]thiophen-3-yl)-2-oxoethyl]thio | 4 | 977.4685 |
| 29 | [2-(benzo[1,3]dioxol-5-yl)-2-oxoethyl]thio | 4 | 965.479 |
| 30 | [2-[[(2-aminopyridin-3-yl)carbonyl]amino] ethyl]thio | 8 | 966.5189 |
| 31 | [2-[[3,4-dimethoxybenzoyl]amino]ethyl]thio | 8 | 1010.5401 |

EXAMPLE 32

Preparation of compound of formula I where R1 is [2-[6-amino-8-[(3-pyridinylmethyl)amino]-9H-purin-9-yl]ethyl]thio (I-32)

A] Preparation of 6-Amino-8-bromo-9-(2-hydroxyethyl)-9H-purine

To a solution of 10 g (55.8 mmol) 6-amino-9-(2-hydroxyethyl)-9H-purine in 200 ml 0.5M CH$_3$COONa/CH$_3$COOH buffer (pH 4) were added 4 ml of bromine. The reaction mixture was stirred for 8 hours at room temperature. The precipitate was isolated, washed with water and crystallized from ethanol to give 6.13 g (43%) of the desired product.

B] Preparation of 6-Amino-9-(2-hydroxyethyl)-8-[(3-pyridinylmethyl)amino]-9H-purine A mixture of 0.387 g (1.5 mmol) 6-amino-8-bromo-9-(2-hydroxyethyl)-9H-purine and 0.456 3-picolylamine (4.2 mmol) was heated to 150° C. under an argon atmosphere. After completion of the reaction (~5 hours) the reaction mixture was diluted with water leading to the precipitation of the product. The precipitate was isolated, washed with water and diethylether to give 0.372 g (87%) of the desired product.

B] Preparation of 6-Amino-9-(2-chloroethyl)-8-[(3-pyridinylmethyl)amino]-9H-purine A mixture of 350 mg (1.22 mmol) 6-amino-9-(2-hydroxyethyl)-8-[(3-pyridinyl-methyl)amino]-9H-purine and 2 ml of thionylchloride was stirred at 50° C. After completion of the reaction (~3h) the mixture was concentrated in vacuo and subsequently diluted with water and the pH was adjusted to pH 7 with ammonia. The precipitate was isolated, washed with water, ethyl acetate and diethylether to give 197 mg (53%) of the desired product. $^1$H-NMR (DMSO): 8.62 (s, 1H), 8.44 (d, 1H), 7.92 (s, 1H), 7.80 (d, 1H), 7.38 (t, 1H), 7.33 (m, 1H, NH), 6.32 (s, 2H, $NH_2$), 4.60 (d, 2H), 4.34 (t, 2H), 3.92 (t, 2H).

The title compound I-32 was prepared starting from 6-amino-9-(2-chloroethyl)-8-[(3-pyridinyl-methyl)amino]-9H-purine and IX-4 (compound of formula IX wherein $Rp_1$ is acetyl, $Rp_2$ is hydrogen and $Rp_4$ is methyl) according to example 4 steps D-E. MS(ESI): 1070.5701.

EXAMPLE 33

Preparation of compound of formula I where R1 is [2-[(3-cyclopentyloxy-4-methoxyphenyl)amino]ethyl]thio (I-33)

A] Preparation of (2-Chloroethyl)(3-cyclopentyloxy-4-methoxyphenyl)amine

To a solution of 2.15 g (10.4 mmol) 3-cyclopentyloxy-4-methoxyaniline (*J. Org. Chem.* 2005,70, 1050) in 100 ml methanol were added 2.0 g (14.1 mmol) chloroacetaldehyde solution (55% in water), 3.9 g (62.6 mmol) $NaBH_3CN$ and 0.5 ml acetic acid. The reaction was stirred over night at 15° C. and the solvent was subsequently evaporated. The residue was taken up in 120 ml dichloromethane and the organic phase was washed with brine, dried over $Na_2SO_4$ and evaporated in vacuo. The crude product was purified by chromatography on silica gel (hexane:ethyl acetate 100:1 then 15:1) to give 1.78 g (63.5%) of the desired product as a yellow oil. $^1$H-NMR (DMSO): 6.70 (d, 1H), 6.28 (s, 1H), 6.06 (d, 1H), 5.43 (m, 1H), 4.69 (m, 1H), 3.68 (m, 2H), 3.60 (m, 3H), 3.32 (m, 2H), 1.83 (m, 2H), 1.69 (m, 4H), 1.55 (m, 2H).

The title compound I-33 was prepared starting from (2-chloroethyl)(3-cyclopentyloxy-4-methoxyphenyl)amine and IX-4 (compound of formula IX wherein $Rp_1$ is acetyl, $Rp_2$ is hydrogen and $Rp_4$ is methyl) according to example 4 steps D-E.

EXAMPLE 34

Preparation of compound of formula I where R1 is [2-[(4-pyridinylmethyl)amino]ethyl]thio (I-34)

B] Preparation of compound of formula VII where R1 is [2-[(4-pyridinylmethyl)amino]ethyl]thio and $Rp_1$ and $Rp_2$ are benzoyl To a solution of 163 mg (0.15 mmol) of the product of step A of example 8 in 3 ml methanol were added 0.0146 ml (0.15 mmol) 4-pyridinecarbaldehyde, 0.0442 ml acetic acid and 7.8 mg $NaBH_3CN$. The mixture was stirred over night at room temperature and subsequently diluted with 30 ml ethyl acetate. The organic layer was washed with sat. aqueous $NaHCO_3$ and brine, dried over $Na_2SO_4$, filtered and concentrated in vacuo. The crude product was purified by flash chromatography on silica gel ($DCM:MeOH:NH_3$ 100:0:0.01→96:4:0.01) to afford the desired product as a white solid.

The title compound I-34 was prepared starting from the product of step A example 34 according to example 8 step C. MS(ESI): 937.5300.

EXAMPLE 35

Modulation of Neutrophil Elastase Production

Human neutrophils are isolated by applying whole heparinized blood to a Histopaque column and collecting the granulocytes by centrifugation. The activity of a compound of the invention (A compound of Formula I), hereinafter referred to as test compound, is established by mixing the test compound (50 µM) in standard phosphate buffered saline containing 2.5% (w/v) bovine serum albumin and 0.8 mM SAAVNA with cytochalasin B (5 mg/L) and approximately $10^6$ neutrophil cells. The total volume of the reaction mixture is 0.8 mL and concentrations specified are the final concentrations in the mixture. After 10 minutes incubation at 37° C./5% $CO_2$, the reaction is initiated by the addition of fMLP (0.1 µM) and the mixture is incubated for 30 minutes at 37° C./5% $CO_2$ before measuring the absorption at 405 nm. Neutrophil preparations from blood from 3 different donors were used in parallel. All samples were measured in duplicate. Results are given as % repression of activation of neutrophils in the following Table 5.

TABLE 5

| Test compound | Average repression of activation (%) |
| --- | --- |
| Example 1 | 19 ± 0.6 |
| Example 4 | 31 ± 2.4 |
| Example 11 | 20 ± 0.97 |
| Erythromycin | 5 ± 0.30 |
| Clindamycin | 4 ± 0.07 |
| Tetracycline | −17 ± 0.30 |

EXAMPLE 36

Inhibition of Phosphodiesterase 3 (PDE-3)

Phosphodiesterase 3 was isolated from human platelets (Weishaar, R. E., Burrows, S. D., Kobylarz, D. C., Quade, M. M. and Evans, D. B. (1986), Biochem. Pharmacol., 35:787). The test compound, reference compound or water (control) are added to a buffer containing 40 mM Tris-HCl (pH 7.8), 3 mM $MgCl_2$, 1 mM DTT, 0.01% BSA, 200 mM $NH_4Cl$, 0.1 µM cAMP and 0.1 µCi [$^3$H]cAMP.

Thereafter, the reaction is initiated by addition of the enzyme (final amount depending on the efficiency of the isolation) and the mixture is incubated for 30 min at 30° C. For basal control measurements, the enzyme is omitted from the reaction mixture Following incubation, the reaction is stopped by heating the plate to 60° C. for 3 min after which time SPA beads are added. After 20 min at 22° C. under shaking, the amount of [$^3$H]5'AMP is quantified with a scintillation counter (Topcount, Packard). The data was used to calculate $IC_{50}$ values summarized in table 6.

TABLE 6

| Test compound | $IC_{50}$ ($PDE_3$) (µM) |
| --- | --- |
| Example 1 | 0.32 |
| Example 4 | 1.90 |
| Example 11 | 0.23 |
| Erythromycin | >10 |

EXAMPLE 37

Inhibition of Phosphodiesterase 4 (PDE4)

Phosphodiesterase 4 was isolated from human monocytes (U-937 cells), (Torphy, T. J., Zhou, H. L. and Cieslinski, L. B. (1992), J. Pharmacol. Exp. Ther., 263:1195). The test compound, reference compound or water (control) are added to a buffer containing 40 mM Tris/HCl (pH 7.8), 3 mM $MgCl_2$, 1 mM DTr, 0.01% BSA, 200 mM $NH_4Cl$, 1 µM cAMP and 0.1 µCi [$^3H$]cAMP.

Thereafter, the reaction is initiated by addition of the enzyme (final amount depending on the efficiency of the isolation) and the mixture is incubated for 30 min at 30° C. For basal control measurements the enzyme is omitted from the reaction mixture. Following incubation, the reaction is stopped by heating the plate to 60° C. for 3 min, after which time SPA beads are added. After 20 min at 22° C. under shaking, the amount of [$^3H$]5'AMP is quantified with a scintillation counter (Topcount, Packard). The data was used to calculate $IC_{50}$ values summarized in table 7.

TABLE 7

| Test compound | $IC_{50}$ ($PDE_4$) (µM) |
|---|---|
| Example 1 | 0.71 |
| Example 4 | 5.80 |
| Example 11 | 0.23 |
| Erythromycin | >10 |

EXAMPLE A

A cream (o/w) of the following composition was manufactured in the usual manner:

| Active substance | 1.0 g |
|---|---|
| Emulsifying cetostearyl alcohol | 9.0 g |
| Liquid paraffin | 10.5 g |
| Vaseline | 10.5 g |
| Water | 69.0 g |

EXAMPLE B

An ointment (w/o) of the following composition was manufactured in the usual manner:

| Active substance | 1.0 g |
|---|---|
| Wool (lanolin) alcohols | 3.0 g |
| Cetostearyl alcohol | 0.25 g |
| Vaseline | 46.75 g |
| Water | 49.0 g |

EXAMPLE C

An ethanolic gel of the following composition was manufactured using procedures familiar to those skilled in the art:

| Active substance | 1.0 g |
|---|---|
| Butylated hydroxytoluene | 0.02 g |

| Hydroxypropylcellulose | 2.0 g |
|---|---|
| Ethanol 99.5% | 96.98 g |

What is claimed is:

1. An antibiotic macrolide compound of the general formula I:

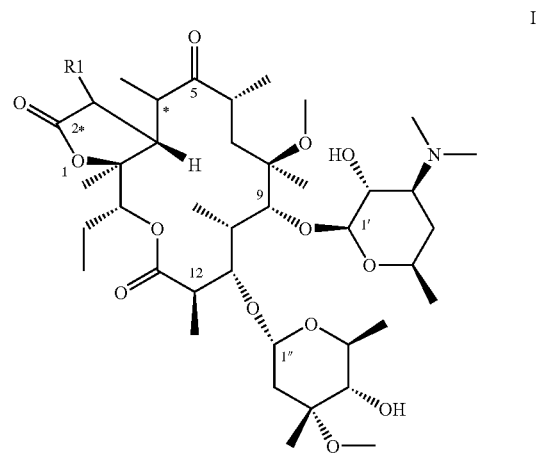

wherein
R1 is a residue —Y—X-Q;
Y is S, SO or $SO_2$;
X is a bond or a linear group with up to 9 atoms consisting of C, N, O and/or S, of which up to 2 atoms can be N, one atom can be O or S, one carbon atom can appear as a CO group, one sulphur atom can appear as an $SO_2$ group and two adjacent C atoms can be present as —CH═CH— or —C≡C—;
Q is hydrogen, alkyl, heterocyclyl or aryl;
* indicates a chiral centre which is in the (R) or (S) form; or pharmaceutically acceptable acid addition salts or in vivo cleavable esters thereof.

2. The antibiotic macrolide of claim 1, wherein Y is S or $SO_2$.

3. The antibiotic macrolide of claim 2, wherein Y is S.

4. The antibiotic macrolide of claim 1, wherein X is $(CH_2)_n$, $(CH_2)_mOCH_2$, $(CH_2)_2NCH_3(CH_2)_2$, $CH_2CH_2NH$, or $(CH_2)_pCOW$, where n and p are 1-3, m is 0-3 and W is absent or O or NH.

5. The antibiotic macrolide of claim 4, wherein Y is S and X is selected from the group consisting of ethyl, propyl, $CH_2CO$, $CH_2COCH_2$, $CH_2CONR$, $CH_2CONRCH_2$, $CH_2CONRCH_2CH_2$, $CH_2CH_2CONR$, $CH_2CH_2CONRCH_2$, $CH_2CH_2NR$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH$═$CH$ or $CH_2C$≡$C$;
where R in the above expressions is hydrogen or methyl.

6. The antibiotic macrolide of claim 4, wherein X is ethyl or propyl.

7. The antibiotic macrolide of claim 1, wherein Q is hydrogen, alkyl or a group of the following formula

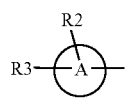

wherein

is a phenyl ring or a x-membered saturated or unsaturated heterocyclo-aliphatic or heteroaromatic ring containing from 2 to (x-1) carbon atoms with x being 5 or 6, and from 1 to 3 hetero atoms selected from the group consisting of nitrogen, oxygen and sulfur, R2 and R3 are independently selected from the group consisting of hydrogen, alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted alkyl groups, cyano, nitro, amino, alkylamino, dialkylamino, alkylthio, mercapto, hydroxy, carbamoyl, a carboxyl group, an oxo group; or aryl or heterocyclyl, which may be unsubstitued or substituted with one or more of the above identified substituents other than aryl or heterocyclyl, or when both substituents R2 and R3 are located at adjacent carbon atoms of the ring

these two substituents can be taken together with said adjacent carbon atoms to form a 5 to 6 membered aromatic or a x-membered saturated or unsaturated heterocycloaliphatic or heteroaromatic ring containing from 2 to (x-1) carbon atoms with x being 5 or 6, and from 1 to 3 hetero atoms selected from the group consisting of nitrogen, oxygen and sulfur, wherein Q can have alltogether one to four substituents of the kind as defined for R2 and R3.

8. The antibiotic macrolide of claim 7, wherein Q is selected from the group consisting of:

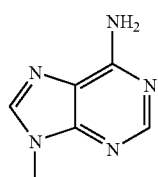 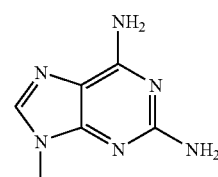

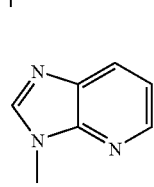 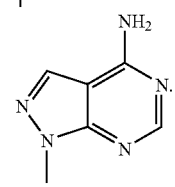

9. The antibiotic macrolide of claim 7, wherein R1 is selected from the group consisting of:

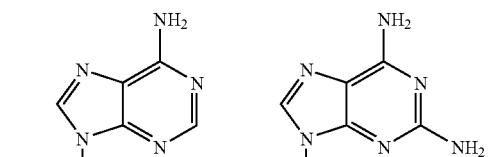

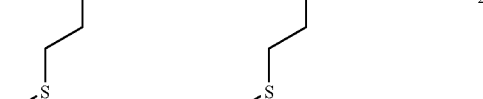

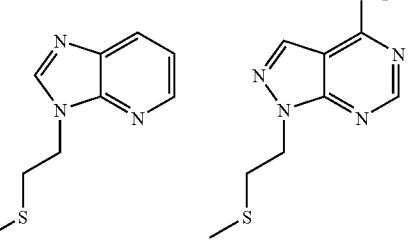

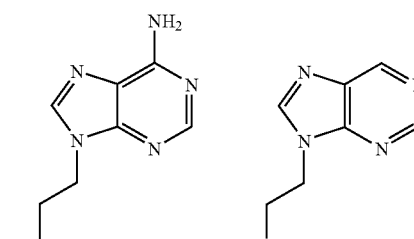

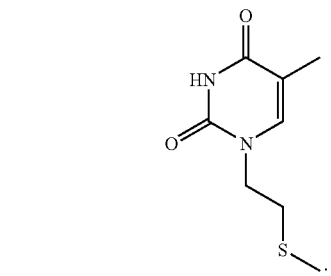

10. The antibiotic macrolide of claim 1 wherein R1 is the following group:

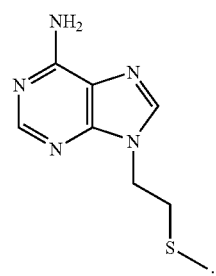

11. The antibiotic macrolide of claim 1 wherein R1 is the following group:

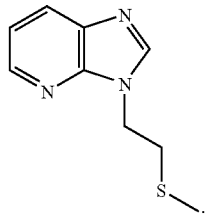

12. The antibiotic macrolide of claim 1 wherein R1 is the following group:

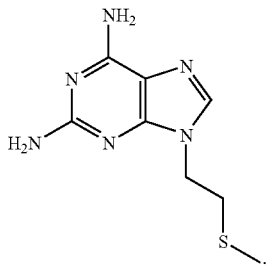

13. The antibiotic macrolide of claim 1 wherein R1 is the following group:

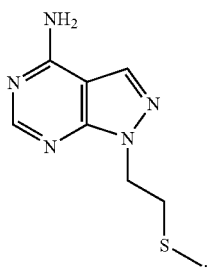

14. The antibiotic macrolide of claim 1 wherein R1 is the following group:

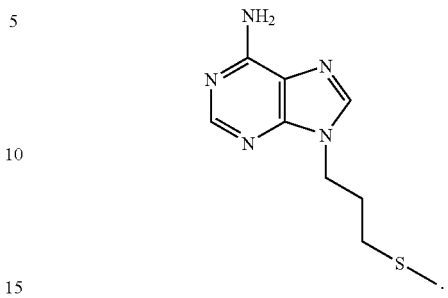

15. A composition comprising an antibiotic macrolide compound of the formula I:

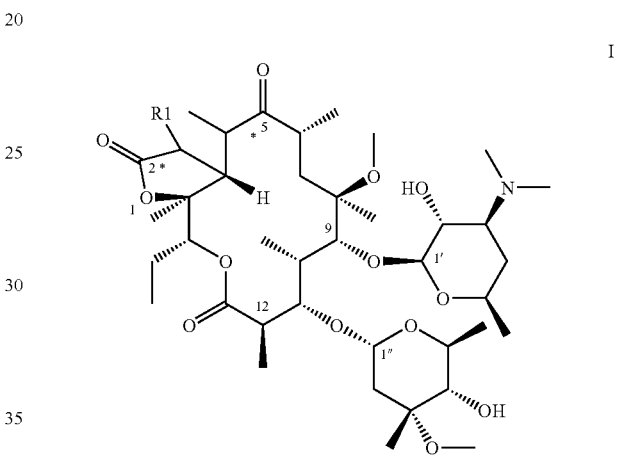

wherein
R1 is a residue —Y—X-Q;
Y is S, SO or SO$_2$;
X is a bond or a linear group with up to 9 atoms consisting of C, N, O and/or S, of which up to 2 atoms can be N, one atom can be O or S, one carbon atom can appear as a CO group, one sulphur atom can appear as an SO$_2$ group and two adjacent C atoms can be present as —CH═CH— or —C≡C—;
Q is hydrogen, alkyl, heterocyclyl or aryl;
* indicates a chiral centre which is in the (R) or (S) form;
or pharmaceutically acceptable acid addition salts or in vivo cleavable esters thereof and a pharmaceutically acceptable carrier.

* * * * *